(12) United States Patent
Pesavento

(10) Patent No.: US 10,835,556 B2
(45) Date of Patent: Nov. 17, 2020

(54) HYDROLYZED TETRAVALENT METAL SALTS AND METHODS OF BIOFILM INHIBITION

(71) Applicant: THE BOARD OF TRUSTEES OF THE UNIVERSITY OF ILLINOIS, Urbana, IL (US)

(72) Inventor: Russell Pesavento, Chicago, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/288,694

(22) Filed: Feb. 28, 2019

(65) Prior Publication Data

US 2019/0262393 A1 Aug. 29, 2019

Related U.S. Application Data

(60) Provisional application No. 62/636,223, filed on Feb. 28, 2018.

(51) Int. Cl.
| | |
|---|---|
| *A61K 33/244* | (2019.01) |
| *A61K 9/14* | (2006.01) |
| *A61L 27/54* | (2006.01) |
| *A61Q 11/00* | (2006.01) |
| *A61L 31/16* | (2006.01) |
| *A61K 33/00* | (2006.01) |
| *A61L 29/16* | (2006.01) |

(52) U.S. Cl.
CPC .............. *A61K 33/244* (2019.01); *A61K 9/14* (2013.01); *A61K 33/00* (2013.01); *A61L 27/54* (2013.01); *A61L 29/16* (2013.01); *A61L 31/16* (2013.01); *A61Q 11/00* (2013.01); *A61L 2300/102* (2013.01); *A61L 2300/404* (2013.01); *A61L 2300/606* (2013.01)

(58) Field of Classification Search
CPC ........ A61K 33/244; A61K 33/00; A61K 9/14; A61K 9/006; A61K 33/30; A61K 33/06; A61K 33/38; A61K 33/36; A61K 33/24; A61L 31/16; A61L 27/54; A61L 2300/102; A61L 2300/606; A61L 2300/404; A61Q 11/00; A01N 59/20; A01N 59/16; A01N 59/06; A61P 31/04
See application file for complete search history.

(56) References Cited

PUBLICATIONS

Farias et al, Antimicrobial Activity of Cerium Oxide Nanoparticles on Opportunistic Microorganisms: A Systemic Review, Hindawi Biomed Research International., 14 pages. (Year: 2018).*
Masadeh et al, Cerium Oxide and Iron Oxide Nanoparticles Abolish the Antimicrobial Activity of Ciprofloxacin Against Gram Positive and Gram Negative Biofilm Bacteria, Cytotechnology,, 67: 427-435 (Year: 2015).*

(Continued)

*Primary Examiner* — Carlos A Azpuru
(74) *Attorney, Agent, or Firm* — Thomas | Horstemeyer, LLP

(57) ABSTRACT

Described herein are hydrolyzed tetravalent salts and formulations thereof that can be used to inhibit a biofilm. Also described herein are uses of the hydrolyzed tetravalent salts and formulations thereof to inhibit a biofilm and/or treat biofilm infection.

18 Claims, 12 Drawing Sheets

S. aureus HL2003, BHI media: Post-wash wells (12 hours growth)
Col. I - 200 µM CeO$_2$ (Avg Rh = 4nm)- 49% Biofilm inhibition (negative control last well of Col. 1)
Col. II - 200 µM ZrCl$_4$- 74% Biofilm inhibition (negative control last well of col. II)
Col. III - 200 µM TiCl$_4$-2THF (Avg Rh = 7.8 nm) -68% biofilm inhibition (negative control last well of Col. III)
Col. IV - 400 µM THF-no inhibition (negative control last well of Col. IV)
Col. V - 800 µM KCl- no inhibition (negative control last well of Col. V)
Col. VI - positive control (BHI, cells, 2% glucose) no inhibitor added, bottom row is the negative control. (negative control last well of Col. VI)

(56) References Cited

PUBLICATIONS

Pelletier, Effects of Cerium Oxide Nanoparticles on Bacterial Growth and Viability, Applied and Environmental Microbiology, pp. 7981-7989. (Year: 2010).*

Algburi et al., "Control of Biofilm Formation: Antibiotics and Beyond," Appl. Environ. Miorobiol. 2017, 83:e02508-02516.

Allaker et al., "Nanoparticles and the control of oral infections," Int. J. Antimicrob. Agents. 2014, 43:95-104.

Belfield et al., "Do orally administered antibiotics reach concentrations in the middle ear sufficient to eradicate planktonic and biofilm bacteria? A review," Int. J. Pediatr. Otorhinolaryngol. 2015, 79:296-300.

Bowen, "Effectiveness of Professionally-Applied Silver Diamine Fluorite in Arresting Dental Caries," J. Dent. Hygiene. 2016, 90:75-78.

Chu et al., "The effectiveness of the biannual application of silver nitrate solution followed by sodium fluoride varnish in arresting early childhood caries in preschool children; study protocol for a randomised controlled trial," Trials. 2015, 16:article No. 426.

Cobrado et al. "In vivo antibiofilm effect of cerium, chitosan and hamamelitannin against usual agents of catheter-related bloodstream infections," J. Antimicrob. Chemother. 2013, 68:126-130.

Cobrado et al., "Cerium, chitosan and hamamelitannin as novel biofilm inhibitors?" J. Antimcirob. Chemother. 2012, 67:1159-1162.

Crystal et al., "Parental perceptions and acceptance of silver diamine fluoride staining," J. Am. Dent. Assoc. 2017, 148:510-518.

Das et al., "Cerium oxide nanoparticles: applications and prospects in nanomedicine," Nanomedicine (Future Medicine). 2013, 8:1483-1508.

Davies, "Understanding biofilm resistance to antibacterial agents," Nat. Rev. Drug Discov. 2003, 2:114-122.

Davis et al., "Isolation of silver- and antibiotic-resisistant Enterobacter cloacae from teeth," Oral Microbiol. Immunol. 2005, 20:191-194.

Demars et al., "Revisiting the solution structure of ceric ammonium nitrate," Angew. Chem. Int. Ed. Engl. 2015, 54:7354-7358.

Dewhirst et al., "The human oral microbiome," J. Bacteriol. 2010, 192:5002-5017.

Farias et al., "Antimicrobial Activity of Cerium Oxide Nanoparticles on Opportunistic Microorganisms: A Systematic Review," Biomed. Res. Int., 2018, article ID 1923606.

Ferretti et al., "Susceptibility of Streptococcus mutans to antimicrobial agents," Antimicrob. Agents Chemother. 1976, 10:274-276.

Fritz et al., "Muciprocin and Chlorhexidine Resistance in Staphylococcus aureus in Patients with Community-Onset Skin and Soft Tissue Infections," Antimicrob. Agents Chemother. 2013. 57:559-568.

Hannig et al., "Nanomaterials in preventive dentistry," Nat. Nanotechnol. 2010, 5:565-569.

Heller et al., "Microbial Diversity in the Early In Vivo-Formed Dental Biofilm,"Appl. Environ. Microbiol. 2016, 8:1881-1888.

Inkielewicz-Stepniak et al., "Pharmacological and toxicological effects of co-exposure of human gingival fibroblasts to silver nanoparticles and sodium fluoride," Int. J. Nanomedicine, 2014, 9:1677-1687.

Jaramillo et al., "Hematogenous Osteomyelitis in Infants and Children: Imaging of a Changing Disease," Radiology, 2017, 283:629-643.

Kim, "Colonizing features of Staphylococcus aureus in early childhood atopic dermatitis and in mothers: a cross-sectional comparative study done at four kindergartens in Daegu, South Korea," Ann. Allergy Asthma Immunol. 2011, 106:323-329.

Klein et al., "Streptococcus mutans-derived extracellular matrix in cariogenic oral biofilms," Front. Cell Infect. Microbiol. 2015, 5:10.

Lakhani et al., "Staphylococcal Skin Infections in Children," Pediatr. Drugs. 2005, 7:77-102.

Li et al.,"Effect of Antimicrobial Interventions on the Oral Microbiota Associated with Early Childhood Caries," Pediatr. Dent., 2015, 37:226-244.

Lister et al., Frontiers in Cellular and Infection Microbiology. 2014, 4:178.

Masedeh et al., "Cerium oxide and iron oxide nanoparticles abolish the antibacterial activity of ciprofloxacin against gram positive and gram negative biofilm bacteria," Cytotechnology. 2015, 67:427-435.

Mijnendonckx et al., "Antimicrobial sliver: uses, toxicity and potential for resistance," Biometals. 2013, 26:609-621.

Nabavi et al., "Surface-Chemistry of Nanometric Ceria Particles in Aqueous Dispersions," J. Colloid. Interf. Sci. 1993, 160:459-471.

Negrini et al., "Staphylococcus aureus Contamination in a Pediatric Dental Clinic," J. Clin Pediatr. Dent., 2009, 34:13-18.

O'Toole, "Microtiter dish biofilm formation assay," J. Vis. Exp. 2011, 47:e2437); abstract only.

Pelletier et al., "Effects of engineered cerium oxide nanoparticles on bacterial growth and viability," Appl. Environ. Microbiol. 2010, 76:7981-7989.

Peterson et al., "The Dental Plaque Microbiome in Health and Disease," PLoS One. 2013, 8:e58487.

Pettinger et al., "Crystallization kinetics of cerium oxide nanoparticles formed by spontaneous, room temperature hydrolysis of cerium(iv) ammonium nitrate in light and heavy water," Phys Chem. Chem. Phys. 2017, 19:3523-3531.

Rabin et al., "Agents that inhibit bacterial biofilm formation," Future Med. Chem. 2015, 7:647-671.

Rajeshkumar et al., "Synthesis and biomedical applications of Cerium oxide nanoparticles—A Review," Biotechnol. Rep. 2018, 17:1-5.

Ren et al., "Inhibition of Streptococcus mutans polysaccharide synthesis by molecules targeting glycosyltransferase activity," J. Oral Microbiol. 2016, 8:article No. 31095.

Roberts et al., "Oral biofilms: a reservoir of transferable, bacterial, antimicrobial resistance," Expert Rev. Anti. Infect. Ther., 2010, 8:1441-1450.

Saini et al., "Biofilm: A dental microbial Infection," J. of Nat. Sci., Biol. Med. 2011, 2:71-75.

Shah et al., "Antibacterial Activity of Polymer Coated Cerium Oxide Nanoparticles," PLoS One. 2012, 7:e47827.

Silva-Dias et al., "In vitro antifungal activity and in vivo antibiofilm activity of cerium nitrate against Candida species," J. Antimicrob. Chemother. 2015, 70:1083-1093.

Xu et al., "CeO2 Nanocrystals: Seed-mediated synthesis and size control," Mater. Res. Bull. 2008, 43:990-995.

Xu et al., "Cerium oxide nanoparticle: a remarkably versatile rare earth nanomaterial for biological applications," NPG Asia Materials. 2014, 6:e90.

Xu et al., "Mechanistic understanding of cerium oxide nanoparticle-mediated biofilm formation in Pseudomonas aeruginosa," Environ. Sci. Pollut. Res. Int. 2018, 25:34765-34766.

* cited by examiner

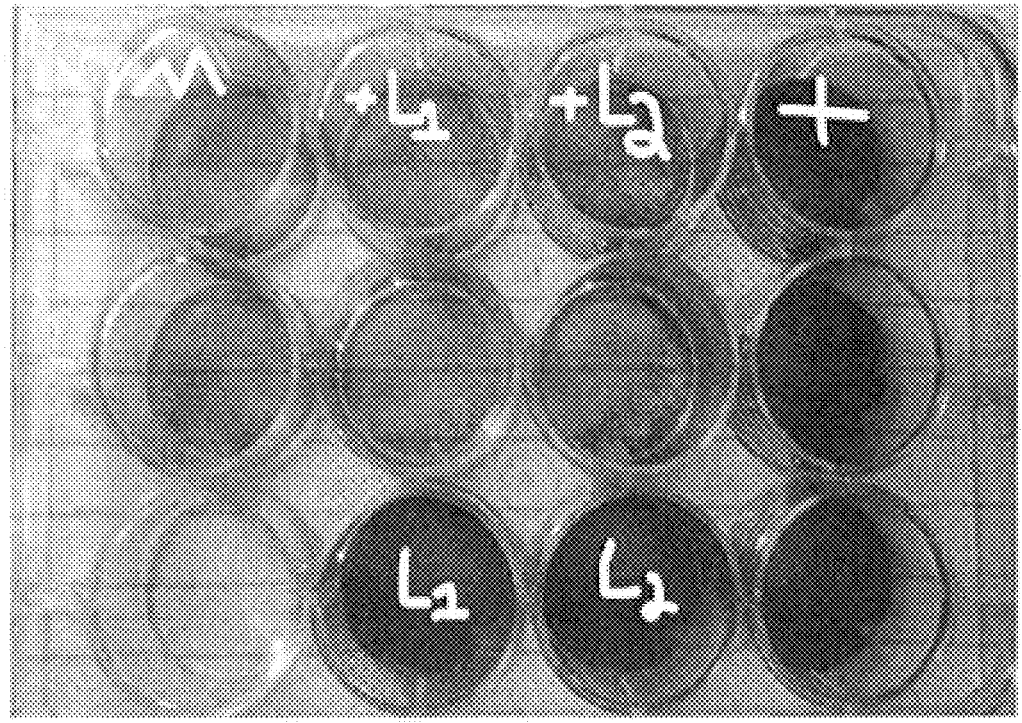

S. Mutans UA159, BHI media: Post-wash wells

(M) - 200 µM $CeO_2$ (Avg $R_h$ =4 nm) – 48% Biofilm inhibition last well is negative (BHI, no cells)

(+L1) - 200 µM $CeO_2$ (Avg $R_h$ =4 nm) + 4 Eq. $NaAsO_2Me_2$ – 71% biofilm inhibition (L1 = 4 Eq. $NaAsO_2Me_2$ alone, no biofilm inhibition)

(L2+)- 200 $CeO_2$ (Avg $R_h$ =4 nm) + 4 Eq. Picolinic acid n-oxide- 44% biofilm inhibition (L2 = 3 Eq. Picolinic acid N-oxide alone, no biofilm inhibition)

(+) - positive control (BHI, cells, 1% sucrose) no inhibitor added

FIG. 1

S. Mutans UA159, BHI media: Post-wash wells
Col. I - 200 uM $CeO_2$ (4 nm) 33% Biofilm inhibition
Col. II - 200 µM CeO2 (10-20 nm, Alfa Aesar purchased) No Biofilm inhibition
Col. III - negative control (BHI, no cells)
Col. IV - positive control (BHI, cells, 1% sucrose) no inhibitor added

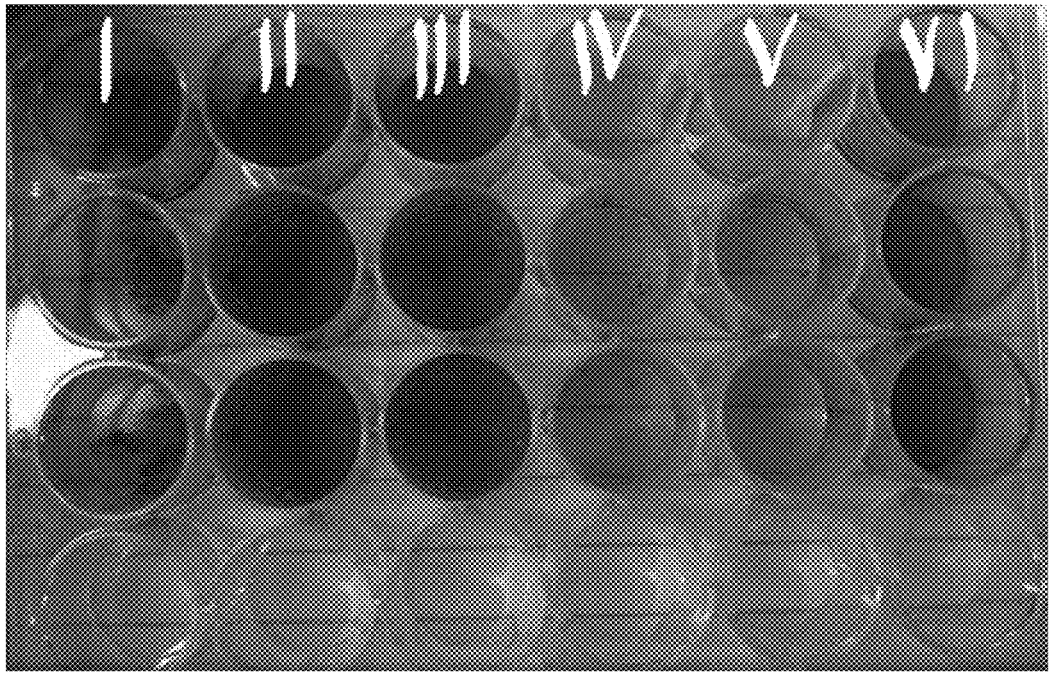

S. Mutans UA159, BHI media: Post-wash wells (6-8 hours growth)

Col. I - 200 µM $CeO_2$ (4 nm) – 44 % Biofilm inhibition
Col. II - 200 µM $CeO_2$ (4 nm) + 0.5 -1.0 Eq. $Ce(NO_3)_3$ – No Biofilm Inhibition
Col. III - 200 µM $CeO_2$ (4 nm) + 0.5-1.0 Eq. $La(NO_3)_3$ – 14% Biofilm Inhibition
Col. IV - 200 µM $CeO_2$ (4 nm) + 0.5-1.0 Eq. $MgCl_2$ – 78% Biofilm Inhibition
Col. V - 200 µM $CeO_2$ (4 nm) + 0.5-1.0 Eq. $CaCl_2$ – 81% Biofilm Inhibition
Col. VI - positive control (BHI, cells, 1% sucrose) no inhibitor added, bottom row is the negative control.

FIG. 3

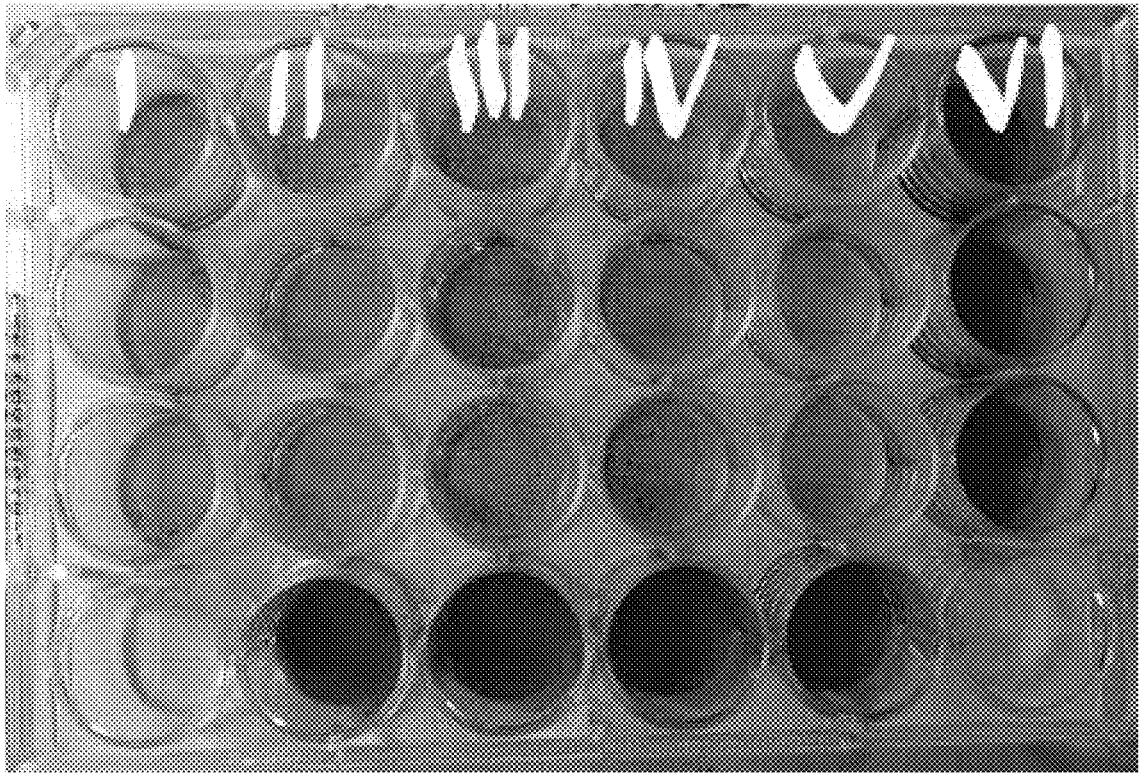

S. mutans UA159, BHI media: Post-wash wells (6-8 hours growth)

Col. I - 200 µM $CeO_2$ (4 nm) – 44% Biofilm Inhibition (negative control last well of Col. I)

Col. II - 200 µM $CeO_2$ (4 nm) + 1 Eq. $Ca(NO_3)_2$ – 65% Biofilm Inhibition / $Ca(NO_3)_2$ no activity Col. III - 200 µM $CeO_2$ (4 nm) + 1 Eq. $Mg(NO_3)_2$ – 61% Biofilm Inhibition / $Mg(NO_3)_2$ no activity Col. IV - 200 µM $CeO_2$ (4 nm) + 1 Eq. $Sr(NO_3)_2$ – 69% Biofilm Inhibition / $Sr(NO_3)_2$ no activity Col. V - 200 µM $CeO_2$ (4 nm) + 1 Eq. $ZnCl_2$ – 75% Biofilm Inhibition / $ZnCl_2$ no activity Col. VI - positive control (BHI, cells, 1% sucrose) no inhibitor added, bottom row is the negative control. (negative control last well of Col. VI)

FIG. 4

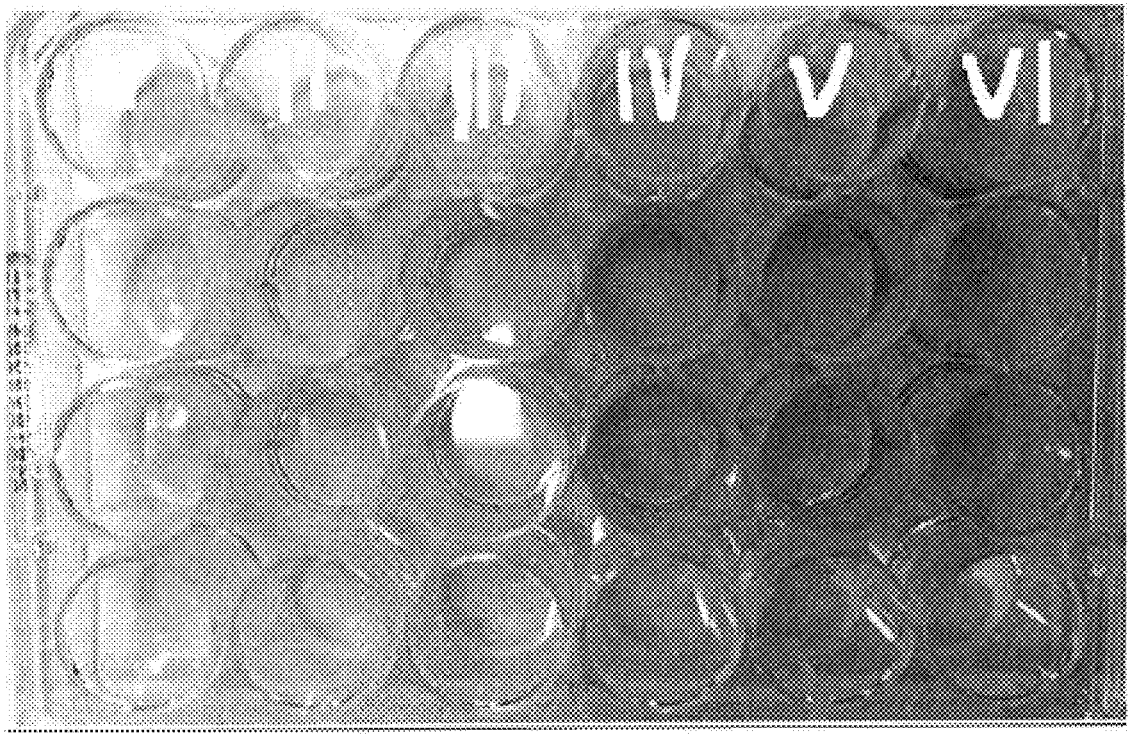

S. aureus HL2003, BHI media: Post-wash wells (12 hours growth)

Col. I - 200 µM $CeO_2$ (Avg Rh = 4nm)- 49% Biofilm inhibition (negative control last well of Col. 1)

Col. II - 200 µM $ZrCl_4$- 74% Biofilm inhibition (negative control last well of col. II)

Col. III - 200 µM $TiCl_4$-2THF (Avg Rh = 7.8 nm) -68% biofilm inhibition (negative control last well of Col. III)

Col. IV - 400 µM THF-no inhibition (negative control last well of Col. IV)

Col. V - 800 µM KCl- no inhibition (negative control last well of Col. V)

Col. VI - positive control (BHI, cells, 2% glucose) no inhibitor added, bottom row is the negative control. (negative control last well of Col. VI)

FIG. 5

| Strain–atmosphere culture: BHI, 37°C, 20h | $OD_{600}$ | growth w/ 1mM CAN | growth w/ 1mM CAS | growth w/ 1mM $AgNO_3$ |
|---|---|---|---|---|
| S. mutans UA159- 5% $CO_2$ | 0.010 | ++ | ++ | -- |
| S. sobrinus 6175- 5% $CO_2$ | 0.010 | ++ | ++ | -- |
| S. aureus Newman-aerobic | 0.020 | ++ | ++ | -- |
| E.coli BW25113-aerobic | 0.015 | ++ | ++ | -- |
| B. subtilus str168-aerobic | 0.020 | ++ | ++ | -- |

+Control      CAS      3 nm      10-20 nm      30nm

HYDROLYZED TETRAVALENT METAL SALTS AND METHODS OF BIOFILM INHIBITION

CROSS-REFERENCE TO RELATED APPLICATIONS

This application claims the benefit of and priority to U.S. Provisional Patent Application No. 62/636,223, filed on Feb. 28, 2018, entitled "Hydrolyzed Tetravalent Metal Salts as Biofilm Inhibitors," the contents of which is incorporated by reference herein in its entirety.

STATEMENT REGARDING FEDERALLY SPONSORED RESEARCH

This invention was made with Government support 1T32DE018381-01 awarded by the National Institutes of Health. The Government has certain rights in the invention.

BACKGROUND

Biofilms can contribute to antibiotic resistance and chronic bacterial and fungal infections. As such, there exists a need for compositions and formulations that can inhibit biofilms.

SUMMARY

Described herein are aspects of a pharmaceutical formulation that can be effective to inhibit a biofilm that can include a therapeutically effective amount of a hydrolyzed tetravalent metal salt; and a pharmaceutically acceptable carrier. The hydrolyzed tetravalent metal salt can be a hydrolysis product of a Ce(IV) salt, a Zr(IV) salt, or a Ti(IV) salt. The hydrolyzed tetravalent metal salt can be present as a mononuclear complex, an oligomer, a polymer, or a nanoparticle. The hydrolyzed tetravalent metal salt can be a hydrolysis product of Ce(IV) salt. The hydrolyzed tetravalent metal salt can be $CeO_2$. The $CeO_2$ can be formulated as nanoparticles. The nanoparticles can have an average hydrodynamic radius of about 2-10 nm or less. The pharmaceutical formulation can include an additional metal salt selected from the group consisting of: salts of Ca(II), Sr(II), Ba(II), Zn(II), Cu(II), Be(II), Ni(II), Fe(II), Co(II), Mn(II), Cr(II), V(II), Ti(II), Sc(II), Cd(II), Hg(II), cacodylic acid (As) sodium salt, and any combination thereof.

Also described herein are aspects of a method of inhibiting a biofilm in a subject in need thereof that can include administering to the subject in need thereof an amount of a pharmaceutical formulation that can include a therapeutically effective amount of a hydrolyzed tetravalent metal salt; and a pharmaceutically acceptable carrier. The hydrolyzed tetravalent metal salt can be a hydrolysis product of a Ce(IV) salt, a Zr(IV) salt, or a Ti(IV) salt. The hydrolyzed tetravalent metal salt can be present as a mononuclear complex, an oligomer, a polymer, or a nanoparticle. The hydrolyzed tetravalent metal salt can be a hydrolysis product of Ce(IV) salt. The hydrolyzed tetravalent metal salt can be $CeO_2$. The $CeO_2$ can be formulated as nanoparticles. The nanoparticles can have an average hydrodynamic radius of about 2-10 nm or less. The pharmaceutical formulation can further include an additional metal salt selected from the group consisting of: salts of Ca(II), Sr(II), Ba(II), Zn(II), Cu(II), Be(II), Ni(II), Fe(II), Co(II), Mn(II), Cr(II), V(II), Ti(II), Sc(II), Cd(II), Hg(II), cacodylic acid (As) sodium salt, and any combination thereof. The administration can be oral or topical.

Also described herein are aspects of a medical device that can be one or more surfaces partially or completely coated with a formulation, wherein the formulation can include an amount of a hydrolyzed tetravalent metal salt or precursor thereof. The hydrolyzed tetravalent metal salt can be a hydrolysis product of a Ce(IV) salt, a Zr(IV) salt, or a Ti(IV) salt. The formulation can further can include an additional metal salt selected from the group consisting of: salts of Ca(II), Sr(II), Ba(II), Zn(II), Cu(II), Be(II), Ni(II), Fe(II), Co(II), Mn(II), Cr(II), V(II), Ti(II), Sc(II), Cd(II), Hg(II), cacodylic acid (As) sodium salt, and any combination thereof.

Also described herein are aspects of a biofilm resistant medical device that can include one or more surfaces partially or completely coated with a formulation an amount of a hydrolyzed tetravalent metal salt.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1 illustrates results showing how the addition of different compounds can affect $CeO_2$-NP (Avg. $R_h$=2-10 nm) as biofilm inhibiting agents against *S. mutans*. FIG. 1 can demonstrate activity of the $CeO_2$ nanoparticles when metal containing additives (e.g. $NaAsO_2Me_2$) are added to the stock solution.

FIG. 3 illustrates test shows results of a study to examine the effect of metal ions of different charge on biofilm inhibitory activity of $CeO_2$-NP (Avg. $R_h$=2-10 nm) against *S. mutans*.

FIG. 4 illustrates test results showing biofilm inhibition of $CeO_2$-NP (Avg $R_h$=2-10 nm) against *S. mutans* when divalent metal ions are added to the solution.

FIG. 5 illustrates the activity of hydrolyzed tetravalent metal species Ce(IV), Zr(IV) and Ti(IV) as biofilm inhibitors against *S. aureus* (HL20003).

DETAILED DESCRIPTION

Figure 2:
FIG. 2 is a comparison showing the difference in activity between the $CeO_2$-NP (Avg $R_h$=4 nm) described herein and commercially available $CeO_2$ nanoparticles that have a size of between 10 and 20 nm (Avg. $R_h$=10-11 nm) against *S. mutans*.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, chemistry, inorganic chemistry, organic chemistry, biochemistry, physiology, cell biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent, or any other implantable medical device, can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "control" can refer to an alternative subject or sample used in an experiment for comparison purpose and included to minimize or distinguish the effect of variables other than an independent variable.

As used herein, "dose," "unit dose," or "dosage" can refer to physically discrete units suitable for use in a subject, each unit containing a predetermined quantity of the hydrolyzed tetravalent metal salt or formulation thereof and/or a pharmaceutical formulation thereof calculated to produce the desired response or responses in association with its administration.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The term "nanoparticle" as used herein includes a nanoscale deposit of a homogenous or heterogeneous material. Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, the terms "optional" or "optionally" means that the subsequently described event or circumstance can or cannot occur, and that the description includes instances where said event or circumstance occurs and instances where it does not.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "positive control" refers to a "control" that is designed to produce the desired result, provided that all reagents are functioning properly and that the experiment is properly conducted.

As used herein, "preventative" and "prevent" refers to hindering or stopping a disease or condition before it occurs, even if undiagnosed, or while the disease or condition is still in the sub-clinical phase.

As used herein, "Polymers" are understood to include, but are not limited to, homopolymers, copolymers, such as for example, block, graft, random and alternating copolymers, terpolymers, etc. and blends and modifications thereof.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used interchangeably herein, the terms "sufficient" and "effective," can refer to an amount (e.g. mass, volume, dosage, concentration, and/or time period) needed to achieve one or more desired result(s). For example, a therapeutically effective amount refers to an amount needed to achieve one or more therapeutic effects described elsewhere herein.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be therapeutic in terms of a partial or complete cure of a disease, condition, symptom or adverse effect attributed to the disease, disorder, or condition. The term "treatment" as used herein covers any treatment of bacterial infection, fungal infection, including but not limited to those having a related biofilm formation, in a subject, particularly a human and can include any one or more of the following: (a) inhibiting the disease, i.e., arresting its development; and/or (b) relieving the disease, i.e., mitigating or ameliorating the disease and/or its symptoms or conditions. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain. In some embodiment the disease treated can be bacterial infection, fungal infection, including but not limited to those having a related biofilm formation, and inhibiting biofilm formation.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

Discussion

Microbial biofilms contribute significantly to the complexity of treating orofacial and intraoral bacterial infections. Treatment of biofilm-based infections often requires an excessive use of antimicrobial agents in excess of 10-1000 fold times the initial MIC value of the agent (Belfield et al. Int. J Pediatr. Otorhinolaryngol. 2015 March; 79(3):296-300). This "overuse" exposes the microbiome to an overabundance of our most conserved bactericidal and bacteriostatic agents contributing to antimicrobial resistance (Algburi et al. Appl Environ Microbiol. 2017 Jan. 17; 83(3)). This is especially true when treating the oral cavity, where the microbiome diversity is high, biofilms are prevalent and the potential for genetic exchange is maximized (Antibiofilm Agents: From Diagnosis to Treatment and Prevention" Editors: Rumbaugh, Kendra P., Ahmad, Iqbal (Eds.) 2014; Saini et al. J. of Nat Sci., Biol. Med. 2011; 2(1):71-75; and Roberts and Mullany. Expert Rev. Anti. Infect. Ther. 2010 December; 8(12):1441-50).

*Staphylococcus aureus* (*S. aureus*) is a common pathogen in the orofacial (and intraoral) region. *S. aureus* is responsible for 70% of all skin and soft tissue infections (SSTI's) in children and accounts for approximately 20% of all visits to pediatric clinics (Lakhani and Garbash. Pediatr. Drugs. 2005, 7(2):77-102). Research has indicated the primary mode of transmission of *S. aureus* to the skin in children is through the anterior nares via subunal routes (Kim. Ann Allergy Asthma Immunol. 2011 April; 106(4):323-9) with high levels of *S. aureus* present on the tongue (Negrini et al. J. Clin. Pediatr. Dent. 2009 Fall; 34(1):13-8). This places the entire orofacial/intraoral region at risk of infection. Biofilm growth of *S. aureus* is often associated with chronic infection, which can significantly complicate treatment (Lister and Horswill. Frontiers in Cellular and Infection Microbiology. 2014; 4:178). Current clinical recommendations for the treatment of many pediatric soft tissue infections (SSSI's) includes incision and drainage in addition to prescription antibiotics (www.medscape.com). Although *S. aureus* infections are often associated with soft tissue infections, they can also lead to bone infection (e.g., osteomyelitis) where surgery is often indicated when the infection reaches the chronic phase (Jaramillo et al. "Hematogenous Osteomyelitis in Infants and Children: Imaging of a Changing Disease" Radiology: Volume 283: Number 3—June 2017). The overuse of broad spectrum decolonizing agents (e.g., chlorhexidine, mupirocin, etc.) in the management of *S. aureus* infections has led to concerns regarding antimicrobial resistance development (Fitz et al. Antimicrob Agents Chemother. 2013 January; 57(1):559-68). As such, the need for developing a more conservative approach to biofilm based infections regarding all biofilm forming organisms, including *S. aureus* is imperative.

Tooth born biofilms comprising *Streptococcus mutans* are associated with the formation of dental caries (Li and Tanner. Pediatr. Dent. 2015, May-June; 37(3):226-44). In 2013, it was estimated that 50% of children between the ages of 5-9 had at least one cavity, and by the age of 17 that number had climbed to 78% (Peterson et. al. PLoS One. 2013, 8(3):e58487). Dental caries in pediatric patients frequently leads to pulpal necrosis, abscesses, tooth loss and increased complexity of treatment. In many cases, a substantial proportion of the dental decay present in pediatric patients is found in lower socioeconomic classes with limited dental care, (Li and Tanner (2015) and Peterson (2013) where restorative work (e.g., crowns, fillings) are not an option financially. An acceptable treatment alternative to restorative work is the use of topical antimicrobial agents to arrest dental caries and inhibit further biofilm formation. Silver containing reagents (e.g., $AgNO_3$ with topical fluoride and silver diamine fluoride, SDF) have been reported successful in arresting early childhood caries (ECC (Chu et al. Trials. 2015, Sep. 25; 16:426).

The silver ion ($Ag^+$) is well known for its antimicrobial activity against common oral pathogens, including *S. mutans* (Kamar et al. Braz. J Microbiol. 2010, 42:805-811 and Bowden. J. Dent. Hygiene (JDH.) 2016, 90(2):75-78). Although Ag-based agents have been found effective in arresting the progression of dental caries in pediatric patients, they can be clinically challenging to apply due to their inherent chemical instability. The application of silver salts intraorally often results in staining of carious tooth structure and soft tissue (Bowden (2016) especially in the esthetic zone where parents are not accepting of a poor esthetics (Crystal et al. Am. Dent. Assoc. 2017 Apr. 27. pii: S0002-8177(17)30273-8). Recent effort has been directed toward the development of silver nanoparticles (AgNPs) as anti-caries agents/biofilm inhibitors, with the idea of limiting the characteristic "staining" found with other silver containing agents. However, the use of AgNPs is not without potential toxic side effects. In situ toxicity to gingival fibroblasts has been reported when AgNPs of a select size range were co-administered with fluoride (Inkielewicz-Stepniak et al. Int. J. Nanomedicine. 2014, Apr. 2; 9:1677-87). As such, there remains a need for topically applied biofilm inhibiting agents in pediatric oral medicine that is not only effective in inhibiting oral plaque formation, but also esthetic and non-toxic to oral and facial tissue.

*S. aureus* and *S. mutans* are the primary pathogens responsible for orofacial/intraoral infection, particularly in in pediatric patients. Both species produce robust and persistent biofilms that inhabit both the hard and soft tissue, limiting the effectiveness of even the most potent antimicrobials, facilitating bacterial resistance and requiring surgical intervention. Accordingly, there is an urgent need to develop effective biofilm inhibitors where infection is prevalent and the potential for epidemic is high.

With that said, described herein are hydrolysis products of tetravalent metal salts and formulations thereof that can be used as topical biofilm inhibitors for orofacial and/or intraoral use. The hydrolysis products of tetravalent metal salts and formulations thereof that can be used as topical biofilm inhibitors for use on the skin. In some embodiments, the hydrolysis products of tetravalent metal salts and formulations thereof can be considered to be the products of the chemical reaction of a metal ion and water. In some embodiments, hydrolysis products may exist as mononuclear complexes, oligomers/oligomers or nanoparticles (or a combination thereof). In some embodiments, the hydrolysis products of Ce(IV) salts and formulations thereof can be used as biofilm inhibitors. In some embodiments, the hydrolysis products of Ce(IV) salts can be $CeO_2$-NP particles. $CeO_2$-NP particles can have the advantage colorless for esthetic application, lack the non-discriminant bactericidal properties of common topical antimicrobials, have limited evidence of toxicity and are known to possess anti-inflammatory/wound healing capacity not seen in other commonly utilized topical agents.

Also described herein are methods of topically administering the hydrolyzed tetravalent metal salts and formulations thereof to treat oral biofilms. Embodiments of a method of biofilm inhibition in one or more areas of the oral cavity by topical administration of the hydrolyzed tetravalent metal salts and/or formulations thereof are also described herein.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Hydrolyzed Tetravalent Metal Salts and Formulations Thereof

Tetravalent metal salts, as defined above, are precursors to effective biofilm inhibitors (e.g., the hydrolyzed tetravalent metal salts) described herein. When dissolved in water, the tetravalent metal ion species can be present as a mononuclear complex, oligomer or polymer, nanoparticle or a combination thereof.

Described herein are hydrolyzed tetravalent metal salts (e.g. the hydrolysis products of tetravalent metal salts) and formulations thereof. Tetravalent metal salt is any such metal salt (e.g., nitrate, halide, sulfate, etc.) that is in the +4 oxidation state. In some embodiments the hydrolyzed tetravalent metal salt can be Ce(IV), Zr(IV), or Ti(IV). The hydrolysis products of tetravalent metals salts can exist as either mononuclear complexes, oligomers/polymers, nanoparticles or a combination thereof. In some embodiments, the hydrolysis products of tetravalent metals salts can exist as nanoparticles. In some embodiments, the nanoparticles can have an average hydrodynamic radius of approximately 25 nm, 20 nm, 15 nm, 10 nm, 9 nm, 8 nm, 7 nm, 6 nm, 5 nm, 4 nm, 3 nm, 2 nm, 1 nm, or smaller. The hydrolyzed tetravalent metal salts and formulations thereof described herein can, in some embodiments, be substantially colorless.

In some embodiments, $CeO_2$-NP as described herein, can have an average hydrodynamic radius of approximately 2-10 nm or smaller, and can be effective for preventing or inhibiting the formation of biofilm on teeth. In one embodiment, the $CeO_2$-NP are prepared with the use of ceric ammonium nitrate (CAN) or a cerium (IV) sulfate sulfuric acid complex at low concentrations in accordance with literature methods. The low concentration may be approximately 5-10 mmol or less and the mixing time can include immediate addition of water up to several days in solution. The reaction may take place at room temperature, at slightly increased or decreased temperatures. Dynamic light scattering measurements on particles prepared at room temperature show a narrow range of particle sizes near 2-10 nm over several weeks as disclosed in the literature (Pettinger et al. Phys Chem. Chem. Phys. 2017 Feb. 1; 19(5):3523-3531).

In some embodiments, soluble Zr(IV) halides such as $ZCl_4$ can be dissolved in deionized water to prepare a solution containing mononuclear complexes, oligomers/polymers or nanoparticles comprising Zr(IV) that are effective biofilm inhibitors.

In some embodiments, soluble Ti(IV) halides such as $TiCl_4$-tetrahydrofuran complex can be dissolved in deionized water to prepare a solution containing mononuclear complexes, oligomers/polymers or nanoparticles comprising Ti(IV) that are effective biofilm inhibitors.

In some embodiments, the hydrolyzed tetravalent metal salts described herein can be mixed with a metal salt, such as a divalent metal salt in some formulations. Suitable additional metal salts that can be added to the hydrolyzed tetravalent metal salts described herein, include but are not limited to salts of Ca(II), Sr(II), Ba(II), Zn(II), Cu(II), Be(II), Ni(II), Fe(II), Co(II), Mn(II), Cr(II), V(II), Ti(II), Sc(II), Cd(II), Hg(II), and cacodylic acid (As) sodium salt.

Mixtures and formulations of $CeO_2$-NP can contain a suitable metal containing compounds. Mg(II), Ca(II), Sr(II), Ba(II), Zn(II), Cu(II) and cacodylic acid (As) sodium salt all can be included with $CeO_2$ in a formulation that can inhibit *S. mutans* biofilms. Other divalent metal salts including derivatives of Be(II), Ni(II), Fe(II), Co(II), Mn(II), Cr(II), V(II), Ti(II), Sc(II), Cd(II), Hg(II), may also enhance the activity of $CeO_2$ as a biofilm inhibitor.

In some embodiments, the hydrolyzed tetravalent metal salts described herein can be mixed with a metal salt, such as a monovalent metal salt in some formulations. Suitable additional metal salts that can be added to the hydrolyzed tetravalent metal salts described herein, include but are not limited to, salts of Group I elements of the Periodic Table of Elements, Cu(I), Ag(I), and Au(I).

Mixtures and formulations of $CeO_2$-NP can contain a suitable monovalent metal containing compounds. Suitable monovalent metals include, but are not limited to, Group I elements of the Periodic Table of Elements, Cu(I), Ag(I), and Au(I) as well as any salt thereof.

In an embodiment, the hydrolyzed tetravalent metal salts and formulations thereof described herein can (including but not limited to $CeO_2$-containing nanoparticles and formulations thereof) can be effective to inhibit the formation of biofilms that are known to cause infection. Table 1 describes examples of bacteria that can be treated with hydrolyzed tetravalent salts of the current invention.

TABLE 1

*Acetobacter aurantius*
*Acinetobacter baumannii*
*Actinomyces israelii*
*Agrobacterium radiobacter*
*Agrobacterium tumefaciens*
*Anaplasma*
*Anaplasma phagocytophilum*
*Azorhizobium caulinodans*
*Azotobacter vinelandii viridans streptococci*
*Bacillus*
*Bacillus anthracis*
*Bacillus brevis*
*Bacillus cereus*
*Bacillus fusiformis*
*Bacillus licheniformis*
*Bacillus megaterium*
*Bacillus mycoides*
*Bacillus stearothermophilus*
*Bacillus subtilis*
"*Bacillus Thuringiensis*"
*Bacteroides*
*Bacteroides fragilis*
*Bacteroides gingivalis*
*Bacteroides melaninogenicus*
*Prevotella melaninogenica*
*Bartonella*
*Bartonella henselae*
*Bartonella quintana*
*Bordetella*
*Bordetella bronchiseptica*
*Bordetella pertussis*
*Borrelia burgdorferi*
*Brucella*
*Brucella abortus*
*Brucella melitensis*
*Brucella suis*
*Burkholderia*

TABLE 1-continued

*Burkholderia mallei*
*Burkholderia pseudomallei*
*Burkholderia cepacia*
*Calymmatobacterium granulomatis*
*Campylobacter*
*Campylobacter coli*
*Campylobacter fetus*
*Campylobacter jejuni*
*Campylobacter pylori*
*Chlamydia*
*Chlamydia trachomatis*
*Chlamydophila*
*Chlamydophila pneumoniae*
*Chlamydophila psittaci*
*Clostridium*
*Clostridium botulinum*
*Clostridium difficile*
*Clostridium perfringens* (previously called *Clostridium welchii*)
*Clostridium tetani*
*Corynebacterium*
*Corynebacterium diphtheriae*
*Corynebacterium fusiforme*
*Coxiella burnetii*
*Ehrlichia chaffeensis*
*Enterobacter cloacae*
*Enterococcus*
*Enterococcus avium*
*Enterococcus durans*
*Enterococcus faecalis*
*Enterococcus faecium*
*Enterococcus galllinarum*
*Enterococcus maloratus*
*Escherichia coli*
*Francisella tularensis*
*Fusobacterium nucleatum*
*Gardnerella vaginalis*
*Haemophilus*
*Haemophilus ducreyi*
*Haemophilus influenzae*
*Haemophilus parainfluenzae*
*Haemophilus pertussis*
*Haemophilus vaginalis*
*Helicobacter pylori*
*Klebsiella pneumoniae*
*Lactobacillus*
*Lactobacillus acidophilus*
*Lactobacillus bulgaricus*
*Lactobacillus casei*
*Lactococcus lactis*
*Legionella pneumophila*
*Listeria monocytogenes*
*Methanobacterium extroquens*
*Microbacterium multiforme*
*Micrococcus luteus*
*Moraxella catarrhalis*
*Mycobacterium*
*Mycobacterium avium*
*Mycobacterium bovis*
*Mycobacterium diphtheriae*
*Mycobacterium intracellulare*
*Mycobacterium leprae*
*Mycobacterium lepraemurium*
*Mycobacterium phlei*
*Mycobacterium smegmatis*
*Mycobacterium tuberculosis*
*Mycoplasma*
*Mycoplasma fermentans*
*Mycoplasma genitalium*
*Mycoplasma hominis*
*Mycoplasma penetrans*
*Mycoplasma pneumoniae*
*Neisseria*
*Neisseria gonorrhoeae*
*Neisseria meningitidis*
*Pasteurella*
*Pasteurella multocida*
*Pasteurella tularensis*
*Peptostreptococcus*
*Porphyromonas gingivalis*
*Prevotella melaninogenica*

TABLE 1-continued

*Pseudomonas aeruginosa*
*Rhizobium radiobacter*
*Rickettsia*
*Rickettsia prowazekii*
*Rickettsia psittaci*
*Rickettsia quintana*
*Rickettsia rickettsii*
*Rickettsia trachomae*
*Rochalimaea*
*Rochalimaea henselae*
*Rochalimaea quintana*
*Rothia dentocariosa*
*Salmonella*
*Salmonella enteritidis*
*Salmonella typhi*
*Salmonella typhimurium*
*Serratia marcescens*
*Shigella dysenteriae*
"*Spirillum volutans*"
*Staphylococcus*
*Staphylococcus aureus*
*Staphylococcus epidermidis*
*Stenotrophomonas maltophilia*
*Streptococcus*
*Streptococcus agalactiae*
*Streptococcus avium*
*Streptococcus bovis*
*Streptococcus cricetus*
*Streptococcus faceium*
*Streptococcus faecalis*
*Streptococcus ferus*
*Streptococcus gallinarum*
*Streptococcus lactis*
*Streptococcus mitior*
*Streptococcus mitis*
*Streptococcus mutans*
*Streptococcus oralis*
*Streptococcus pneumoniae*
*Streptococcus pyogenes*
*Streptococcus rattus*
*Streptococcus salivarius*
*Streptococcus sanguis*
*Streptococcus sobrinus*
*Treponema*
*Treponema pallidum*
*Treponema denticola*
*Vibrio*
*Vibrio cholerae*
*Vibrio comma*
*Vibrio parahaemolyticus*
*Vibrio vulnificus*
*Wolbachia*
*Yersinia*
*Yersinia enterocolitica*
*Yersinia pestis*
*Yersinia pseudotuberculosis*

As discussed herein the hydrolyzed tetravalent metal salts and mixtures thereof (e.g. those including suitable additional metal salts) can be included in a formulation, such as in a pharmaceutical formulation. As such, also described herein are pharmaceutical formulations contain an amount, such as a therapeutically effective amount, of one or more hydrolyzed tetravalent metal salts or a mixture of one or more hydrolyzed tetravalent metal salts and an additional suitable metal salt, that can be administered to a subject in need thereof or be applied to or otherwise incorporated with a surface of a medical device or prosthetic that can be used by or implanted into a subject in need thereof. The additional metal salt can be a monovalent or divalent metal salt. A medical device can be any device or apparatus that can be implanted into a subject. In some embodiments, the formulations can be suitable for topical administration. In some embodiments, the subject can have, be suspected of having, or susceptible to developing a microbial and/or fungal infection, including but not limited to such infection that can have a related biofilm. In some embodiments, the subject can have, be suspected of having, or susceptible to developing an infection with an organism shown in Table 1.

The pharmaceutical formulations containing a therapeutically effective amount of a hydrolyzed tetravalent metal salt or a mixtures thereof described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of a hydrolyzed tetravalent metal salts or mixtures thereof described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

The pharmaceutical formulations can contain a therapeutically effective amount a hydrolyzed tetravalent metal salt or a mixtures thereof described herein. In some embodiments the pharmaceutical formulations can also include a therapeutically effective amount of an auxiliary agent. In some embodiments, the therapeutically effective amount of a hydrolyzed tetravalent metal salt or a mixtures thereof described herein can range from about 1 µg/kg to about 30 mg/kg. In further embodiments, the therapeutically effective amount can range from 1 ng/g bodyweight to about 0.1 mg/g bodyweight. The therapeutically effective amount can range from about 1 pg to about 10 g. In some embodiments, the therapeutically effective amount can range from about 10 nL to about 30 mL. In some embodiments, the therapeutically effective amount can be about 30 mL. In some embodiments, the therapeutically effective amount can be from about 10 nL to about 1 µL.

In embodiments where there is an auxiliary active agent contained in the pharmaceutical formulation in addition to the hydrolyzed tetravalent metal salt or mixture thereof, the therapeutically effective amount of the auxiliary active agent will vary depending on the auxiliary active agent. In some embodiments, the effective amount of the auxiliary active agent ranges from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

The pharmaceutical formulations described herein may be in a dosage form. The dosage forms can be adapted for administration by any appropriate route. Appropriate routes include, but are not limited to, oral (including buccal or sublingual) topical (including buccal, sublingual, dermal, transdermal), gingival, subgingival. Such formulations may be prepared by any method known in the art. The formulations can also be delivered as a coating applied to a medical device or prosthetic that is implanted or otherwise attached to a subject in need thereof.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of a hydrolyzed tetravalent metal salt or mixture thereof described elsewhere herein.

Where appropriate, the dosage forms described herein can be microencapsulated. The dosage form can also be prepared to prolong or sustain the release of any ingredient. In some embodiments, the targeted effector fusion protein or complex thereof can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the targeted effector fusion protein or complex thereof, auxiliary active ingredient, and/or pharmaceutically acceptable salt thereof can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, pastes and mouth washes.

Dosage forms adapted for nasal or inhalation administration include aerosols, solutions, suspension drops, gels, or dry powders. In some embodiments, the targeted effector fusion protein and/or complex thereof, the composition or formulation containing a targeted effector fusion protein and/or complex thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g. the targeted effector proteins and/or complexes thereof, compositions thereof, and formulations thereof, and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the targeted effector fusion protein and/or complex thereof, the composition or formulation containing a targeted effector fusion protein and/or complex thereof, and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a hydrolyzed tetravalent metal salt or mixture thereof. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the hydrolyzed tetravalent metal salt or mixture thereof, such a dosage form can contain a powder base such as lactose, glucose, trehalose, manitol, and/or starch. In some of these embodiments, the hydrolyzed tetravalent metal salt or mixture thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the hydrolyzed tetravalent metal salt or mixture thereof described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intraosseous, intracavernous, gingival, subginigival, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the hydrolyzed tetravalent metal salt or mixture thereof per unit dose. In some embodiments, the predetermined amount of the hydrolyzed tetravalent metal salt or mixture thereof can be a therapeutically effective amount of the hydrolyzed tetravalent metal salt or mixture thereof, effective to treat or prevent a microbial infection, symptom thereof or biofilm thereof and/or a fungal infection, symptom thereof, or biofilm thereof. In other embodiments, the predetermined amount of the hydrolyzed tetravalent metal salt or mixture thereof can be an appropriate fraction of the therapeutically effective amount of the hydrolyzed tetravalent metal salt or mixture thereof. Such unit doses may therefore be administered once or more than once a day. Such pharmaceutical formulations may be prepared by any of the methods well known in the art.

The compounds and formulations thereof can be administered 1, 2, 3, 4, 5, 6, 7, 8, 9, 10, 11, 12, 13, 14, 15, or more times per day, month, or year.

Methods of Using the Hydrolyzed Tetravalent Metal Salts and Formulations Thereof The hydrolyzed tetravalent metal salts and formulations thereof described herein can have biofilm inhibitory properties that make them beneficial in both medicine and dentistry. Without a robust tooth borne biofilm, the incidence of dental caries and decay can reduced or eliminated. Specifically, $CeO_2$-NP described herein have the additional advantage of not killing surrounding cells. $CeO_2$-NP of this invention do not kill the bacteria that cause dental caries and decay at micromolar concentrations, but they operate by inhibiting the protective biofilm layer that forms around the bacteria. With the biofilm absent or lacking structural integrity due to the presence of the $CeO_2$-NP, dental caries and decay can be inhibited, reduced, and/or eliminated.

In embodiments, the hydrolyzed tetravalent metal salts and formulations thereof described herein can be used to reduce biofilm formation in the human body (not in the oral cavity), in non-human animals, or in objects that come into contact with a subject's body. In embodiments the hydrolyzed tetravalent metal salts and formulations thereof described herein can be used to reduce or eliminate biofilm formation on metal surfaces, such as pipes or machines. This can be applicable in the food, pharmaceutical or a variety of other industries. In an embodiment, the hydrolyzed tetravalent metal salts and formulations thereof described herein can inhibit the formation of biofilms related to *S. mutans, S. soobrinus* or any other organism set forth in Table 1.

Materials and formulations described herein that include the hydrolysis products of tetravalent metals described herein, including, but not limited to, $CeO_2$-NP can be used in a variety of dental applications. For example, they can be applied to tooth structures as a varnish in the treatment of cavities. Materials and formulations that include the hydrolysis products of tetravalent metals described herein, including, but not limited to, $CeO_2$-NP can be used as a component of restorative materials, including glass ionomers, crowns, composite resins, etc. The cerium oxide nanoparticles compounds (and other hydrolyzed tetravalent metals and salts thereof described herein) can be included in mouth washes, mouth rinses and toothpastes. Further, cerium oxide nanoparticles (and other hydrolyzed tetravalent metals and salts thereof described herein) can be useful in oral and periodontal surgery, including during implant placement and for limiting post-operative infections. Materials and formulations that include the hydrolysis products of tetravalent metals described herein, including, but not limited to, $CeO_2$-NP can be useful in the treatment of endodontically treated teeth, similar to the use of $Ca(OH)_2$ as an intracoronal medicament in those teeth, and in operative dentistry as a pulp capping agent similar to Thera-Cal or $Ca(OH)_2$. Materials and formulations that include the hydrolysis products of tetravalent metals described herein, including, but not limited to, $CeO_2$-NP can be useful in the development of removal partial dentures, mouth guards, and occlusal night guards.

Materials and formulations described herein that include the hydrolysis products of tetravalent metals described herein, including, but not limited to, $CeO_2$-NP can be used for skin applications. Chronic infections due to *S. aureus*, MRSA, *E. faecalis* and *S. epidermis* based skin and tissue infections can be treated with the topical application of materials and formulations that include the hydrolysis products of tetravalent metals described herein, including, but not limited to, $CeO_2$ and $CeO_2$. Materials and formulations that include the hydrolysis products of tetravalent metals described herein, including, but not limited to, $CeO_2$-NP can be used to treat the biofilm formation of these and other organisms. Further, the hydrolysis products of tetravalent metals described herein, including, but not limited to, $CeO_2$-NP can also be used as adjuvants to the administration of known antibiotics (e.g., betalactams, tetracyclines, quinolones, flouroquinolones, macrolides, aminoglycosides, etc.) to treat chronic bacterial infections.

Materials and formulations described herein that include the hydrolysis products of tetravalent metals described herein, including, but not limited to, $CeO_2$-NP can also be used to reduce or prevent infections related to other medical devices. These devices include catheters, heart valves, implants, surgical pins, contacts lenses, synthetic vascular grafts, stents, etc. Materials and formulations that include the hydrolysis products of tetravalent metals described herein, including, but not limited to, $CeO_2$-NP can also be used reduce or eliminate infections relating to essentially, anything that comes in contact with the body, including all implantable prosthetic devices like hip, knee and shoulder replacement joints, and even tampons. In some embodiments, the device can be coated with, infused with, or otherwise combined with a hydrolysis product of a tetravalent metal (or tetravalent metal salt) or formulation thereof described herein. In some embodiments, that tetravalent metal (or tetravalent metal salt) is CeIV. In some embodiments, the hydrolysis product is $CeO_2$.

Materials and formulations described herein that include the hydrolysis products of tetravalent metals described herein, including, but not limited to, $CeO_2$-NP can also have industrial uses. The use of biofilm inhibitors can be advantageous in instruments and storage devices in the food industry, cooling towers and heat exchange devices/tubing/pipes in nuclear power facilities and related industries. In some embodiments, the an instrument, storage device, or cooling tower or heat exchange devices, tubing, and/or pipes (e.g. those found in a nuclear power facility or other related industries) can be coated with, infused with, or otherwise combined with a hydrolysis product of a tetravalent metal (or tetravalent metal salt) or formulation thereof described herein. In some embodiments, that tetravalent metal (or tetravalent metal salt) is CeIV. In some embodiments, the hydrolysis product is $CeO_2$.

Materials and formulations described herein that include the hydrolysis products of tetravalent metals described herein, including, but not limited to, $CeO_2$-NP can be used to inhibit microbially influenced corrosion processes of metals as well as wastewater treatment. In some embodiments, pipes, tanks, or other conduit or machinery part that comes in contact with waste water at a wastewater treatment facility can be coated with, infused with, or otherwise combined with a hydrolysis product of a tetravalent metal (or tetravalent metal salt) or formulation thereof described herein. In some embodiments, that tetravalent metal (or tetravalent metal salt) is CeIV. In some embodiments, the hydrolysis product is $CeO_2$.

Materials and formulations described herein that include the hydrolysis products of tetravalent metals described herein, including, but not limited to, $CeO_2$-NP can be used to treat and/or inhibit biofilms that are formed by fungal species, including but not limited to *candida, aspergillus, cryptococcus, microsporum, fonsecaea* species. In one embodiment, $CeO_2$-NP can be used to treat biofilms formed by fungal species, including but not limited to *candida, aspergillus, cryptococcus, microsporum, fonsecaea* species. In some embodiments the fungal biofilm is in the oral cavity or on the skin.

Materials and formulations described herein that include the hydrolysis products of tetravalent metals described herein, including, but not limited to, $CeO_2$-NP can be used to treat a chronic infections, which can include a reduction of the establishment of a microbiome or biofilm.

In one embodiment, $CeO_2$-NP can be used to treat chronic infections, which can include reducing the establishment of a microbiome or biofilm. The infections may be infections of the teeth, bone, skin surfaces, etc. In an embodiment, $CeO_2$-containing nanoparticles may be combined with known antibiotic agents to treat chronic infections.

In one embodiment, the hydrolyzed products of tetravalent metal salts and formulations thereof can be used to treat chronic infections, by reducing the establishment of a microbiome or biofilm. In an embodiment, the tetravalent metal salts can be selected from zirconium (IV) or titanium (IV). The infections may be infections of the teeth, bone or skin surfaces or soft tissue etc. In an embodiment, the hydrolyzed products of Zr(IV) and Ti(IV) salts can be combined with known antibiotic agents to treat chronic infections.

Materials and formulations described herein that include the hydrolysis products of tetravalent metals described herein, including, but not limited to, $CeO_2$-NP can be used to coat the surface of prosthetic devices, including but not limited to: dental implants, dental crowns, including wires and acrylic components of orthodontic appliances. In some embodiments, the hydrolyzed products of Zr(IV) and Ti(IV) salts can be used to coat the surface of prosthetic devices, including but not limited to: dental implants and dental crowns, including wires and acrylic components of orthodontic appliances.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Microbial biofilms contribute significantly to the complexity of treating orofacial and intraoral bacterial infections. Treatment of biofilm-based infections often requires an excessive use of antimicrobial agents in excess of 10-1000 fold times the initial MIC value of the agent (Belfield et al. Int. J Pediatr. Otorhinolaryngol. 2015 March;

79(3):296-300). This "overuse" exposes the microbiome to an overabundance of our most conserved bactericidal and bacteriostatic agents contributing to antimicrobial resistance (Algburi et al. Appl Environ Microbiol. 2017 Jan. 17; 83(3)). This is especially true when treating the oral cavity, where the microbiome diversity is high, biofilms are prevalent and the potential for genetic exchange is maximized (Antibiofilm Agents: From Diagnosis to Treatment and Prevention" Editors: Rumbaugh, Kendra P., Ahmad, Iqbal (Eds.) 2014; Saini et al. J. of Nat Sci., Biol. Med. 2011; 2(1):71-75; and Roberts and Mullany. Expert Rev. Anti. Infect. Ther. 2010 December; 8(12):1441-50).

Silver based compounds have been used in the treatment of biofilm-based infections but suffer staining. Recent effort has been directed toward the development of silver nanoparticles (AgNPs) as anti-caries agents/biofilm inhibitors, with the idea of limiting the characteristic "staining" found with other silver containing agents. However, the use of AgNPs is not without potential toxic side effects. In situ toxicity to gingival fibroblasts has been reported when AgNPs of a select size range were co-administered with fluoride (Inkielewicz-Stepniak et al. Int. J. Nanomedicine. 2014, Apr. 2; 9:1677-87). As such, there remains a need for topically applied biofilm inhibiting agents in pediatric oral medicine that is not only effective in inhibiting oral plaque formation, but also esthetic and non-toxic to oral and facial tissue.

The hydrolysis of cerium (IV) salts such as ceric ammonium nitrate (CAN) leads to well defined nanoparticles with an average radius of approximately 3-4 nm (Pettinger et al. Phys Chem. Chem. Phys. 2017 Feb. 1; 19(5):3523-3531). Reports of $CeO_2$-NP as therapeutic agents including anti-cancer agents, anti-macular degeneration agents and anti-antimicrobial agents have surfaced in recent years (Xu and Qu. NPG Asia Materials (2014) 6, e90; doi:10.1038). A primary reason for the diverse bioactivity of $CeO_2$-NP is the "tunability" of the nanoparticles themselves. The $CeO_2$-NP particle size, surface ion distribution, morphology and agglomeration properties all can be manipulated based upon the synthetic and purification methods employed (Das et al. Nanomedicine (Lond). 2013 September; 8(9):1483-508; Shah et al. PLoS One. 2012; 7(10):e47827; and Nanda. RSC Adv., 2016, 6, 111889). Manipulating these nanoparticle properties can lead to substantial changes in both the biological activity and toxicity properties. While the use of $CeO_2$-NP as an antimicrobial agent has yielded mixed results (Shah (2012)) the study of $CeO_2$-NP as biofilm inhibitors has been limited to a single study (Masedeh et al. Cytotechnology 2015 May; 67(3):427-35). Masedeh and co-workers reported that $CeO_2$-NP exhibited no biofilm inhibition on a panel of both gram negative and gram positive bacteria, including two MRSA strains (Id.). However, the use of $CeO_2$-NP in this particular study was limited to nanoparticles with a size range of 25-50 nm.

Figure 8:
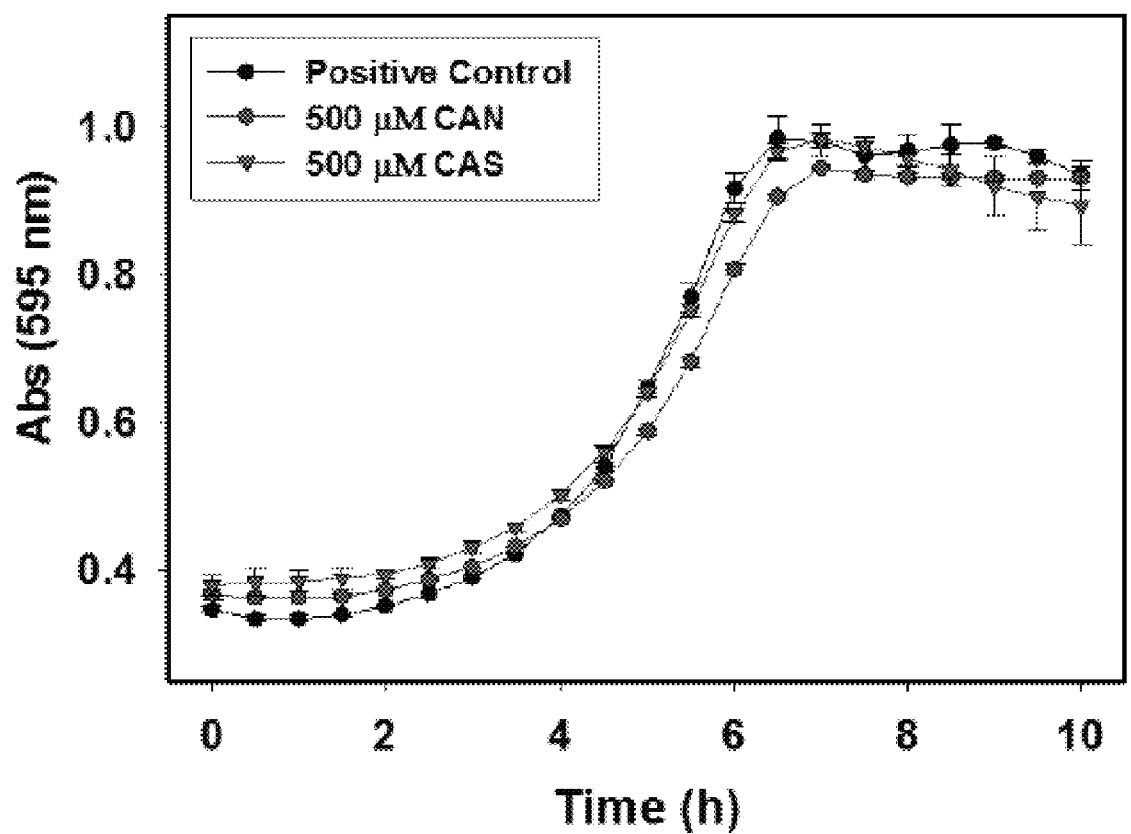
FIG. 8 shows a graph that can demonstrate a Non-inhibitory effect of ceric ammonium nitrate (CAN) and ceric ammonium sulfate (CAS) on the planktonic growth of *S. mutans* in vitro, BHI, 37° C., 5% $CO_2$. Data represents the average UV-Vis absorption of 3 replicates, error bars represent standard deviation.

No study to date has demonstrated biofilm inhibition by $CeO_2$-NP. $CeO_2$-NP utilized in this application have only recently been reported through the hydrolysis of cerium (IV) salts, and are thought to exist primarily in the Ce(IV) oxidation state (Pettinger (2017). The biofilm inhibitory activity of these nanoparticles is significantly more than other forms of $CeO_2$-NP, including 10-20 nm particles, pH 1.5 colloid suspension manufactured by Alfa Aesar. The $CeO_2$-NP of this invention are active for at least 24 hours in vitro in biological media. Growth curve analysis studies indicate that $CeO_2$-NP of this application does not affect the planktonic growth of S. aureus in vitro at concentrations shown to inhibit biofilm formation (FIG. 8). Further, the $CeO_2$-NP are colorless so they can be applied in the orofacial region and the dentition of esthetically conscious patients. Because of the longevity of activity of these particles in nutrient rich liquid broth and without being bound by theory, the $CeO_2$-NP can be co-administered with targeted, narrow spectrum antimicrobial agents for the treatment of biofilm based infections (e.g., methicillin resistant S. aureus, MRSA).

Methods:

Preparation of 2-10 nm (Average $R_h$) $CeO_2$ Nanoparticles.

About 2.7 mg (0.005 moles) of ceric ammonium nitrate (CAN) as added to a small 1 mL vial. About 1 mL of deionized water was added to the vial resulting in a soluble orange solution that faded to colorless over the next 10-20 minutes. The solution was allowed to stand for up to 24 hours at room temperature, at which time the solution was completely colorless with no visibly detectable precipitate. The reaction was traced by UV-Vis spectroscopy, with an increase in the peak at 290 nm over several hours of time and having an average hydrodynamic radius ($R_h$) of approximately 2-10 nm in accordance with literature reports (Pettinger (2017). In another method, the initial dissolution of CAN can produce an immediate yellow-orange solution that can also be added directly to cells/broth, and inhibit biofilm formation.

Preparation of Hydrolyzed Zr(IV) Species.

About 5.8 mg (0.005 moles) zirconium (IV) chloride was added to a 10 mL vial. 5 mL of deionized water was added to the vial (slowly) to solubilize the salt. No color change was evident and the solution remained clear in solution. The solution was allowed to stand for up to 24 hrs. Alternatively, the immediate dissolution of $ZrCl_4$ affords an active species that can be added directly to the cells/broth without standing for hours.

Preparation of Hydrolyzed Ti(IV) Species.

About 8.3 mg (0.005 moles) titanium (IV) chloride-tetrahydrofuran complex was added to a 10 mL vial. 5 mL of deionized water was added to the vial (slowly) to solubilize the salt. The complex was initially a yellow-insoluble material, that gradually gave way to a colorless, soluble solution. The solution was allowed to stand for 24 hrs. Dynamic light scattering of the acidic solution at 5 mM concentration showed the existence of nanoparticles with an average hydrodynamic radius ($R_h$) of approximately 7-8 nm. Alternatively, the dissolution of $TiCl_4$-2THF affords an active species that can be added directly to the cells/broth without standing for hours.

Biofilm Assays.

S. aureus (WT Newman strain) and S. mutans (UA159) and were grown in an overnight culture to log phase growth (OD600=0.5-1.0) in Brain Heart Infusion media (BHI). The cells were diluted by a factor of 100 in BHI media (1-2% glucose or 1% sucrose).

To a 24-well (or 12-well) microtiter plate was added approximately 960 µL of broth inoculated with cells. Biofilm inhibitors ($CeO_2$) were prepared at a concentration of 5 mmol, then added to appropriate wells (40 uL) at a concentration of 200 µM (metal ion) at time zero.

The microtiter plate was either placed in a controlled environment of 37% in the presence of atmospheric oxygen (S. aureus) under static conditions, or then placed in a controlled environment of 37° C., 5% $CO_2$ (S. mutans) under static conditions for 6-8 hours unless specified. The planktonic cells were then removed and the wells were washed with 2-3 mL of DI water, leaving behind the retained biofilm.

A 0.6% crystal violet solution (250-300 µL) was added to each well, and allowed to stand at 37° C. for 1 hour. The wells were washed with 2-3 mLs of DI water then allowed to dry overnight at which time photos were taken.

The adherent biofilm content of each well was quantified by dissolving the purple stained film in each well in 30% acetic acid and measuring the absorbance at 590 nm following appropriate dilution. The average percent biofilm inhibition was then measured against the average of the positive control (in triplicate). The standard deviation was not calculated, but observable from the photos (as each experiment was done in triplicate).

Results

The results from the biofilm assays are shown in FIGS. 1-5. FIG. 1 illustrates results showing how the addition of different compounds can affect $CeO_2$-NP (Avg. $R_h$=2-10 nm) as biofilm inhibiting agents against S. mutans. FIG. 1 can demonstrate activity of the $CeO_2$ nanoparticles when metal containing additives (e.g. $NaAsO_2Me_2$) are added to the stock solution. FIG. 2 is a comparison showing the difference in activity between the $CeO_2$-NP (Avg $R_h$=2-10 nm) described herein and commercially available $CeO_2$ nanoparticles that have a size of between 10 and 20 nm (Avg. $R_h$=10-11 nm) against S. mutans. FIG. 3 illustrates test results showing results of using metal ions of different charges on biofilm inhibitory activity of $CeO_2$-NP (Avg. $R_h$=4-10 nm) against S. mutans. FIG. 4 illustrates test results showing biofilm inhibition of $CeO_2$-NP (Avg $R_h$=2-10 nm) against S. mutans when divalent metal ions are added to the solution. FIG. 5 illustrates the activity of hydrolyzed tetravalent metal species Ce(IV), Zr(IV) and Ti(IV) as biofilm inhibitors against S. aureus (Newman strain).

Example 2

This Example can demonstrate colorless cerium oxide nanoparticles ($CeO_2$-NP)-prepared from Ce(IV) ammonium salts—as a non-bactericidal biofilm inhibitor for dental caries prevention. The use of metal oxide-NP as antimicrobial agents for dental applications has received attention in recent years due to their high surface area and shape irregularities affording them enhanced reactivity. Although the antimicrobial activity, biomedical applications and toxicity of $CeO_2$-NP of different synthetic methodologies have been the subject of conflicting reports, the advantageous and potentially disadvantageous chemical and biological properties of $CeO_2$-NP prepared from Ce(IV) ammonium salts remain largely unexplored. The use of Ce(III) salts (e.g., $Ce(NO_3)_3$) for oral application has been contemplated due to their known biofilm inhibiting properties, anti-erosive effects on extracted teeth and their prior medicinal use. Further, Ce is a member of the lanthanide series of metals known to have high chemical affinity for hydroxyapatite, the primary mineral component found in enamel. However, it is known that metal-oxide NP's have enhanced surface area/chemical reactivity compared to their metal ion constituents as well as the capacity to be "tuned" via the addition of chemical agents that can affect their biological properties.

The use of $CeO_2$-NP as tooth-applied biofilm inhibitors represents a novel step forward in the field of preventive pediatric oral medicine. First, $CeO_2$-NP based chemistries may overcome Ag-related tissue staining, toxicity, disruption of the microbiota and the increased potential of microbial resistance. Second, the suggested NP approach leverages novel biofilm disruption that requires mechanistic definition. Third, the simple chemistry provides affordability and direct translation to solve both the disease and its related social challenges by Ag-stained teeth potentially widespread application. This Example can demonstrate a practical and cost-effective method of introducing a tooth-applied biofilm inhibitor as a preventive treatment to high-risk pediatric populations.

Methods and Results.

In Situ $CeO_2$-NP Preparation from CAN and CAS:

Ceric ammonium nitrate (CAN) and ceric ammonium sulfate (CAS) are commercially available, inexpensive, water-soluble Ce(IV) salts that are used to prepare $CeO_2$-NP of this proposal. Hydrolysis of CAN in dilute aqueous solution at room temperature produces instantaneous, clear dispersions of $CeO_2$-NP crystals with an average NP size of 3.7±0.4 nm and a range of 2-6 nm—with no additional chemical species observed spectroscopically. Dynamic light scattering (DLS) and UV-Vis Spectroscopy (UV-Vis) of 5 mM aqueous solutions of CAN were consistent with the reported in situ formation of $CeO_2$-NP (2). Similarly, CAS hydrolysis yields $CeO_2$-NP with an average hydrodynamic radius $(R_h) \cong 2$ nm via DLS. Deionized water solutions of CAN and CAS (5 mM) were thoroughly mixed and allowed to stand 10-15 min prior to dilution into growth media as described below to ensure complete $CeO_2$-NP formation.

Figure 6:
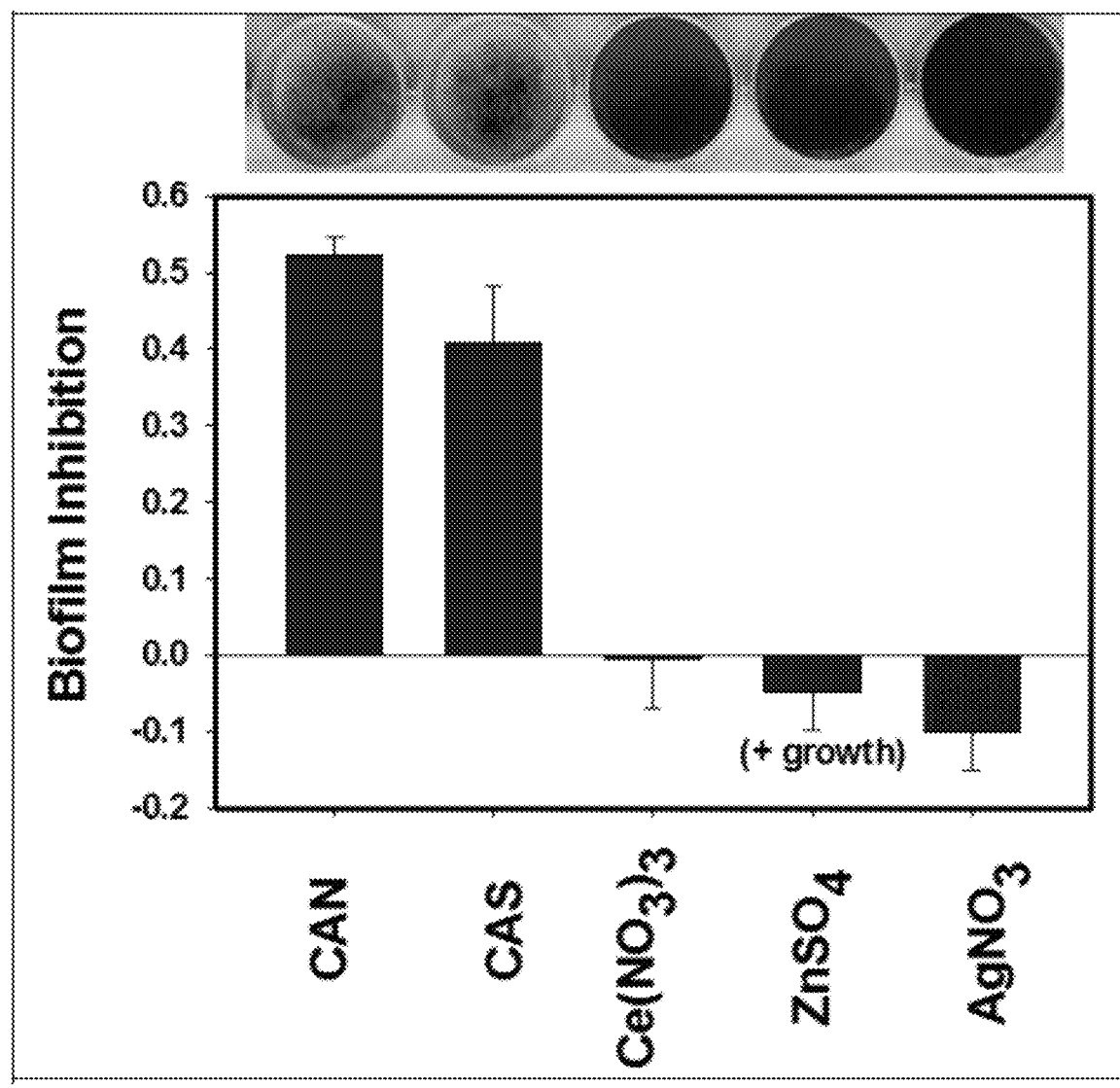
FIG. 6 illustrates an image (top) of crystal violet (CV)-stained wells and a graph (bottom) that can demonstrate the average biofilm inhibition (*S. mutans*) of six replicates at about 125 µM (Metal ion). Error bars represent standard deviation. The purple color in the top image represents adherent *S. mutans* biofilm in each well.

In Vitro Static Biofilm Inhibition:

In vitro static assays were carried out utilizing a 96-well, polystyrene (PS) microtiter plate setup. Cultures of S. mutans and S. sobrinus were grown separately overnight in brain heart infusion (BHI) growth media at 5% $CO_2$, 37° C. Following growth to mid-exponential growth phase (OD600=0.5-0.6), both cultures were diluted 40-fold into a BHI/1% sucrose solution and inoculated into wells of the microtiter plate. Positive controls contained BHI-cell cultures (1% sucrose), whereas test wells further contained 125 µM inhibitor (FIG. 6). Following incubation for 20 h at 5% $CO_2$, 37° C. (conditions known to promote biofilm growth in oral Streptococci) all wells were washed with deionized water and stained with 0.1% crystal violet (CV) dye to visualize and quantify the adherent biofilm in each well. The dyed film was re-dissolved in 30% acetic acid and quantified by UV-Vis absorbance (570 nm) to calculate biofilm inhibition as depicted in Equation I: [Biofilm Inhibition=(Abs+control−Abs inhibitor)/(Abs+control)]. Note the positive control=no inhibitor present.

Figure 7:
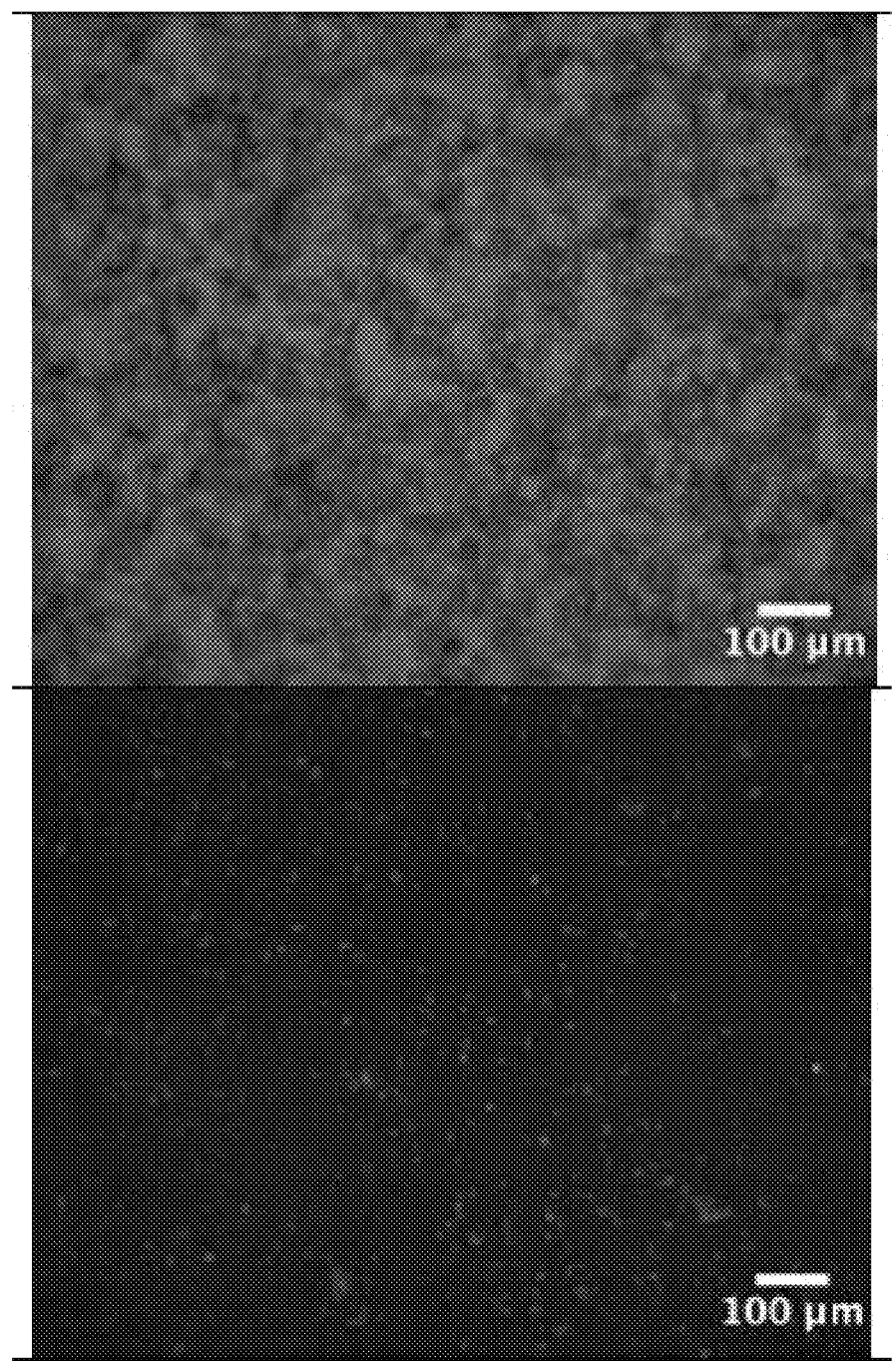
FIG. 7 shows microscopic images of SYPRO™ Ruby biofilm matrix stained microscopic images of *S. mutans* UA159 biofilm growth (20 h, 37° C., 5% $CO_2$, 1% sucrose) (top image) BHI (+control) and (bottom image) BHI (+250 µM CAS).

CAN and CAS significantly outcompeted known biofilm inhibitors $Ce(NO3)3$, $ZnSO_4$ (35) and $AgNO_3$ (all at 125 µM) in the reduction of S. mutans biofilm growth (FIG. 6). CAN inhibited S. mutans biofilm growth by 51% and CAS by 40%, whereas the other agents at the same concentration resulted in a slight increase in biofilm growth. Stained microscopic images (SYPRO™ Ruby Biofilm Matrix stain, Lab-Tek® microscopic chamber well slide) provided additional evidence of CAS induced biofilm reduction of S. mutans (FIG. 7). Further, CAN and CAS both inhibited biofilm formation of S. sobrinus 6715 by 44 and 35%, respectively (not shown). $Ce(NO_3)_3$, $ZnSO_4$ and $AgNO_3$ were all incapable of limiting biofilm growth of S. sobrinus at 125 µM. $AgNO_3$ is currently utilized as a tooth-applied agent for dental caries arrest in pediatric patients. As observed in FIG. 6, sub-inhibitory concentrations of AgNO3 against S. mutans resulted in a slight in increase in biofilm formation whereas the same concentration of CAN and CAS resulted in significant biofilm reduction. It should be noted that both NH4NO3 and $(NH_4)_2SO_4$, by-products of CAN and CAS hydrolysis, respectively, were inactive as biofilm inhibitors against S. mutans at 1 mM. This is evidence that the biofilm inhibition observed from the production of CeO$_2$-NP (from CAN and CAS hydrolysis) is attributed to CeO$_2$-NP and not the by-products of hydrolysis.

Extracellular Mechanism of Biofilm Inhibition:

Potential mechanisms of biofilm inhibition by CeO$_2$-NP were first explored by testing the effect of CAS and CAN on planktonic growth (FIG. 8). Both 500 μM CAS and CAN did not inhibit planktonic growth of S. mutans, although CAN treated cells displayed a slight growth lag vs. the positive control. It is probable that CeO$_2$-NP inhibits biofilm formation via disruption of extracellular or communicative pathways that do not directly involve cell wall damage. To further explore potential extracellular mechanisms of biofilm inhibition, dispersal assays were carried out on existing S. mutans and S. sobrinus biofilms grown statically for 6 h as described above (96-well plate, BHI, 1% sucrose). After 6 h, the planktonic cells were removed, the adherent biofilm rinsed (0.9% NaCl) and replaced with fresh 200 μL BHI (positive control) or BHI/500 μM CAS (test wells). All wells were allowed to incubate an additional 6 h after which the adherent biofilm was washed, stained and quantified via UV-Vis analysis (37). Biofilm dispersal was calculated similar to inhibition in Equation I via UV-Vis. At 500 μM CAS, only a minimal dispersal effect on biofilms produced by S. mutans (6%) and S. sobrinus (8%) was observed. This can suggest the mechanism of biofilm inhibition by CeO$_2$-NP is not solely due to chemical disruption of the biofilm matrix, but rather, it likely targets an early event in cellular attachment or biofilm initiation.

Figures 9, 10:
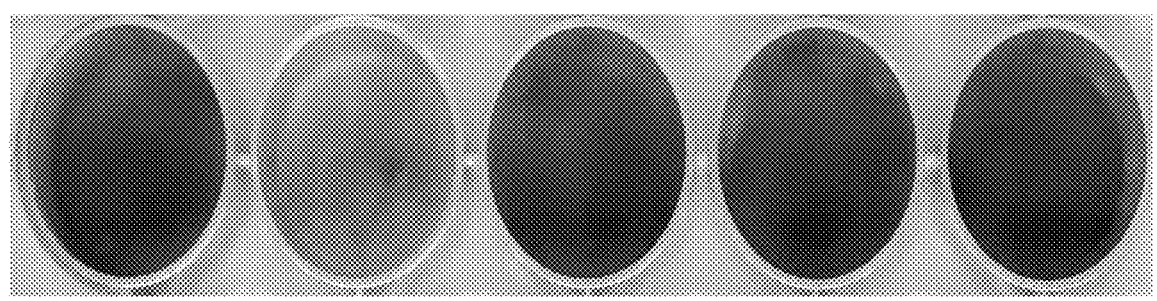
FIG. 9 shows a table that and demonstrate the effect of CAN, CAS and $AgNO_3$ on in vitro planktonic growth of bacteria under the conditions listed in the table of FIG. 9.
FIG. 10 shows an image of 0.1% CV stained PS wells of both untreated and cerium agent treated (125 µM Ce) biofilm growth of S. mutans. Retention of CV stain is proportional to adherent biofilm. No significant inhibition was observed with commercially available $CeO_2$-NP.

Bacterial Exposure:

Tooth application may involve exposure to bacteria outside the oral cavity, including the skin and digestive system. CAN, CAS and AgNO$_3$ (1 mM-metal) were tested for their effect on in vitro planktonic growth of bacteria under the conditions listed in FIG. 9. CAN and CAS allowed visible growth (++) in all strains of bacteria tested, whereas exposure to 1 mM AgNO$_3$ under the same conditions prevented visible (--) growth in the same strains. The non-bactericidal nature of CeO$_2$-NP combined with the ineffectiveness in biofilm dispersion may result in less disturbance of the microbiota. Presumably, the optimal mode of tooth-application of CeO$_2$-NP in high caries risk pediatric patients is post dental cleaning at a dental office or a school sponsored outreach program.

Example 3

Biofilm growth is responsible for 80% of all bacterial infections (1) and a decrease in antimicrobial efficacy of up to 1000-fold (2, 3). The composition of medically relevant biofilms varies significantly de-pending on both the tissue and host. The oral cavity is home to a diverse array of microbiota, estimated to encompass approximately 700 species. (4) Group B Streptococci (GBS) are robust biofilm formers found on the tooth surface in both early and mature biofilm development (5). One of the principle species responsible for biofilm induced tooth decay is S. mutans (6), also a risk factor for bacterial endocarditis. S. mutans has long been the target of antimicrobial therapy (7). However, topically applied bactericidal agents (Ag salts) that inhibit tooth decay are often non-selective and have raised concerns of bacterial resistance via repeated application (8, 9). Thus, topically applied biofilm inhibitors with non-lethal mechanisms of action have been proposed as the preventive treatment of choice (10).

Cerium oxide nanoparticles (CeO$_2$-NP) have attracted both dental (11, 12) medicinal (13) interest because they possess a wide scope of biological activity attributed to variations in synthetic methodology (14). The antimicrobial activity of CeO$_2$-NP has been recently reviewed and activity was found to increase with decreasing NP size (15). However, only two published studies to date has focused on the interaction of CeO$_2$-NP with various strains of bacteria under biofilm forming conditions (in vitro). Masadeh concluded that CeO$_2$-NP domain size 25-50 nm) were not active as biofilm inhibitors on a panel of gram positive and negative bacteria. (16) Xu concluded that 50 nm commercially available CeO$_2$-NP had a net biofilm increasing effect in the presence of by P. aeruginosa (17) Because the bioactivity of CeO$_2$-NP is dependent upon several factors (e.g. size, morphology, etc.) we sought to expand upon these studies.

The direct hydrolysis of Ce(IV) salts under dilute conditions have been shown to produce CeO$_2$-NP at room temperature (18, 19). Ceric ammonium nitrate (CAN) hydrolysis was recently shown to produce acidic dispersions of CeO$_2$-NP crystals with an average domain size of 3.7±0.4 nm and a range of 2-6 nm (20), although high concentrations of CAN in nitric acid produces only a dimeric structure (21). The below equation (1) summarizes the hydrolysis of CAN under dilute (mmol) conditions (Equation 1):

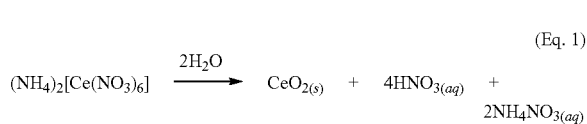

(Eq. 1)

Dynamic light scattering (DLS) measurements of 5 mM aqueous solutions of CAN in 10 mmol NaCl supported the reported NP formation (20). Similar results were obtained with 5 mM CAS in 10 mM NaCl, although a second peak was identified at a much larger size attributed to aggregation (see e.g., Methods and FIG. 11).

The initial goal was to screen the in vitro biofilm inhibiting properties of aqueous dispersions of both CAN and CAS compared to commercially available CeO$_2$-NP of size and storage. In vitro static biofilm inhibition assays were carried out utilizing polystyrene (PS) microtiter plates according to a general literature protocol (22). Briefly, S. mutans UA159 cultures were grown to exponential growth phase (OD$_{600}$=0.5-0.6) and diluted with BHI (1% sucrose). Test wells were inoculated with BHI (1% sucrose), cultured cells and each inhibitor. Following a 20-hr incubation period at 37° C. and 5% CO$_2$, all wells were gently rinsed to remove debris and non-adherent cells. The wells were then stained with 0.1% crystal violet (cv) dye for 30 minutes, washed with water and air dried. Biofilm quantification was achieved by dissolving the adherent material with 33% acetic acid and measuring the absorbance (570 nm) via UV-Vis Spectroscopy.

Figure 14:
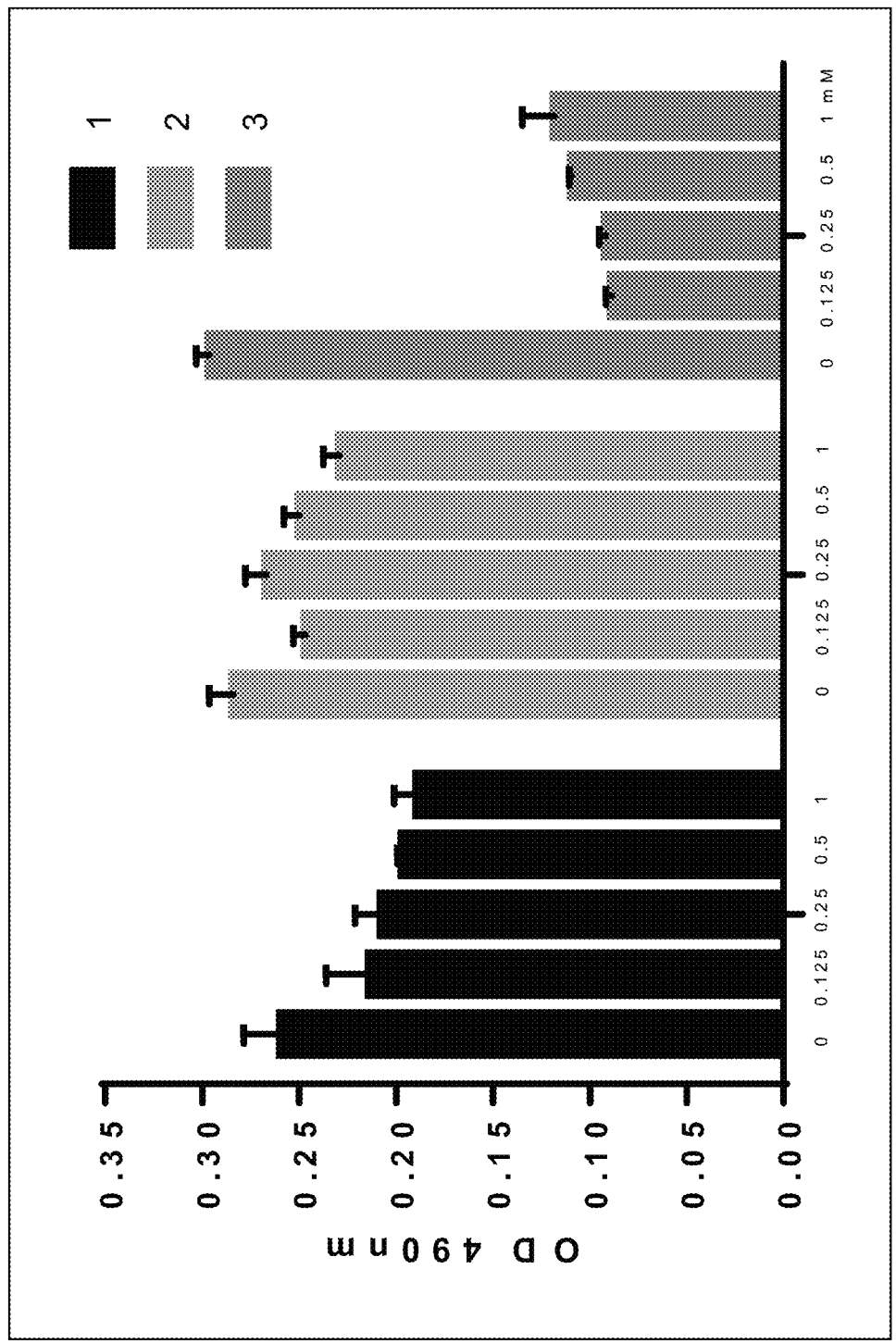
FIG. 14 shows a graph that can demonstrate toxicity data from immortalized gingival keratinocytes. (1) is Cerium Ammonium Nitrate, (2) Cerium Ammonium Sulfate, (3) Silver Nitrate.

The initial screen of biofilm inhibiting activity was carried out utilizing 125 μM Ce for each Ce-based reagent, and 1 mM ammonium nitrate and ammonium sulfate. Both CAN and CAS displayed significant inhibition of biofilm formation (≅40%) of S. mutans (see e.g., Methods and FIG. 12). No biofilm inhibition was observed at 1 mM NH$_4$NO$_3$ or (NH$_4$)$_2$SO$_4$. Commercial dispersions of CeO$_2$-NP: 3 nm solution diameter (Strem, stored at pH 3.5), 10-20 nm solution diameter (Alfa Aesar, stored at pH 1.5) and 30 nm powder diameter (Alfa Aesar stored as an acidic dispersion) had no significant effect on biofilm formation in S. mutans (FIGS. 7A-7B and 10) at 20 h of growth. Cerium (III) nitrate has previously been shown to inhibit both bacterial and yeast biofilm formation (23-25), but was inactive in the current study. Light microscopy with fluorescent labeling also supported ceric ammonium salt disruption of *S. mutans* biofilm formation. A Lab-Tek® microscopic chamber well slide containing *S. mutans* and growth media, both treated and untreated, was incubated for 20 hrs under the above conditions. SYPRO™ Ruby Biofilm Matrix Stain (Invitrogen) was used to stain the adherent biofilm post-incubation. Reduction adherent biofilm cells was found in the treated wells (250 µM CAS) (FIGS. 7A-7B and 10) vs non treated wells. Further, 500 µM (Ce) CAN had a slight lagging effect the planktonic growth rate of *S. mutans* while CAS produced a non-significant growth effect (FIG. 8) This suggests the biofilm inhibiting effects are not attributed to growth delays or inhibition in the planktonic phase. FIG. 14 shows a graph that can demonstrate toxicity data from immortalized gingival keratinocytes. (1) is Cerium Ammonium Nitrate, (2) Cerium Ammonium Sulfate, (3) Silver Nitrate. FIG. 14 can demonstrate the reduced toxicity $CeO_2$-NP derived from CAN and CAS hydrolysis have on human telomerase immortalized gingival keratinocytes as compared to treatment with $AgNO_3$ in DermaLife K keratinocyte culture media. Cells were incubated for 24 h with varying concentrations of test agents and cellular metabolic activity was quantified via the MTS assay.

Figure 13:
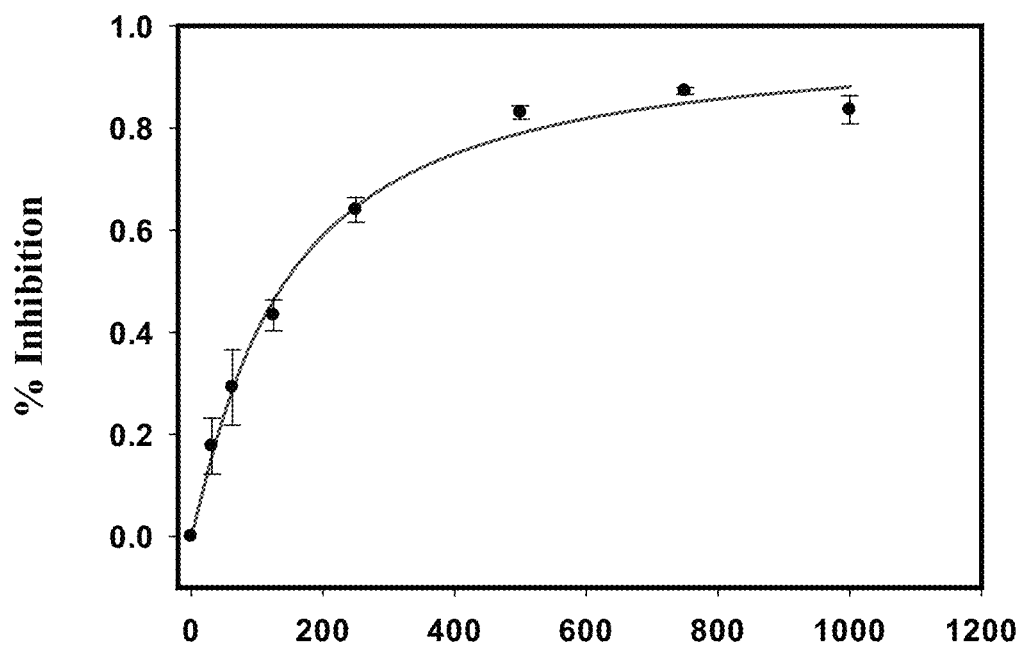
FIG. 13 shows a graph that can demonstrate a dose response curve of biofilm formation in S. mutans UA159 with CAN in BHI at 37° C., 5% $CO_2$ for 20 hrs growth. The 50% inhibitory concentration ($IC_{50}$) value is 137±24 µM CAN.

To quantify the in vitro biological potency of CAN as a biofilm inhibiting agent, a dose response study was carried out (Methods and FIG. 13). In a similar manner as described above, *S. mutans* UA159 was grown in BHI (1% sucrose) on a 96-well PS microtiter plate over a range of CAN concentrations for 20 hr. A half-inhibitory concentration ($IC_{50}$) of 137 µM (Ce) was experimentally determined for the biofilm inhibition of *S. mutans*. Both NH4NO3 and $(NH_4)_2SO_4$, products of ceric salt hydrolysis, were not active in limiting planktonic growth or disrupting bio-film formation. In addition, 125 µM $Ce(NO_3)_4$, shown to produce nanoceria under dilute aqueous conditions (18), had a similar biofilm inhibitory activity against *S. mutans* as compared to CAN confirming the non-contributory role of the ammonium ion (results not shown)

Methods

Preparation, Analysis of Ceric Ammonium Salts Solutions.

Figure 11:
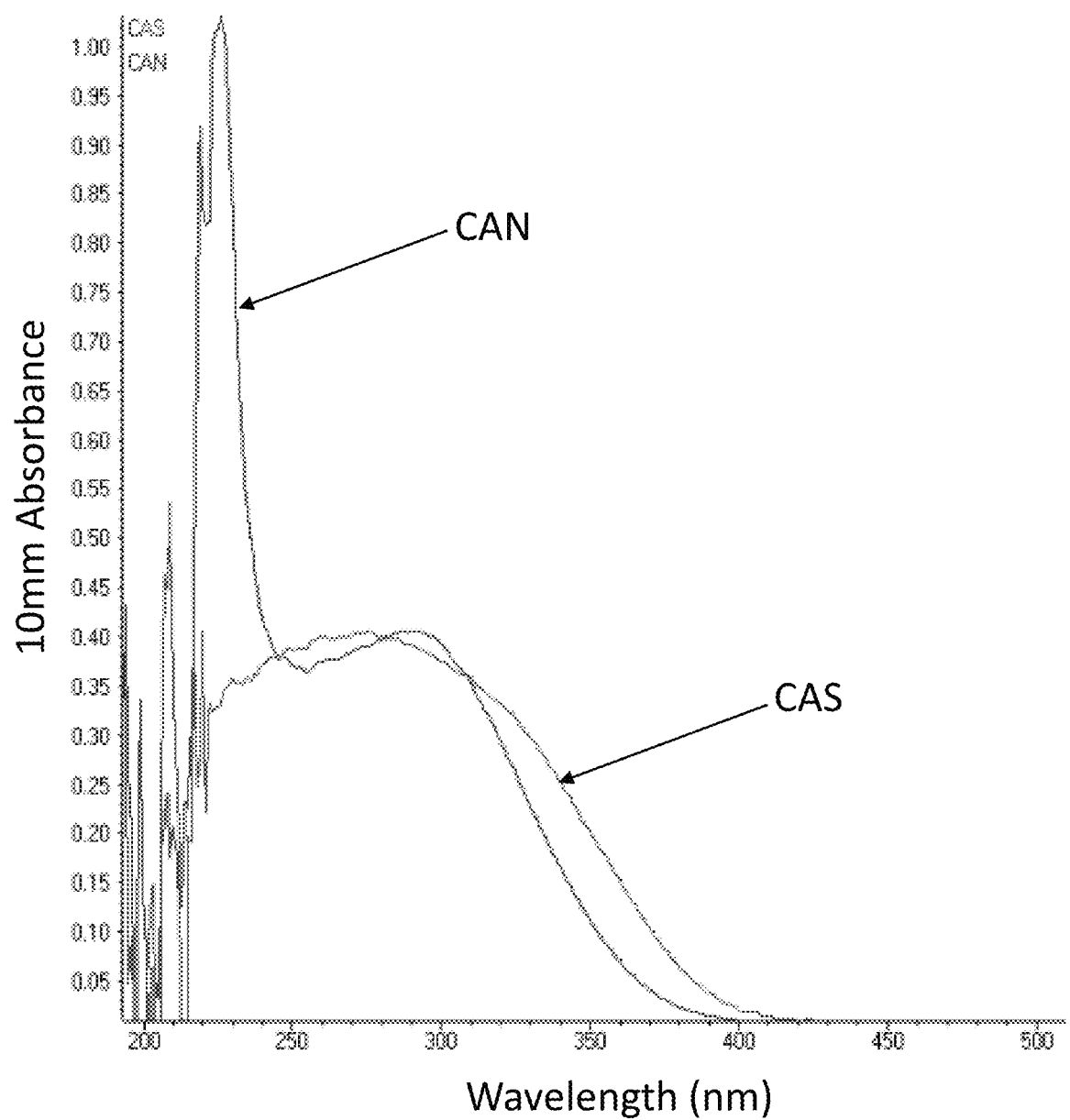
FIG. 11 shows a graph that can demonstrate UV-Vis Absorption Spectra of 100 µM CAS and CAN in $H_2O$ at room temperature. The solutions were allowed to stand for 4 hours after hydrolysis of each solution at 5 mM Ce. The intense peak below 250 nm in CAN is attributed to nitrate absorbance.

Ceric ammonium nitrate (Aldrich, 13.7 mgs) (CAN) was dissolved in 5.0 mL of deionized water at room temperature to afford a 5 mM (Ce) stock solution. The faint-orange colored solution faded within minutes with gently mixing. The microtiter plate wells were loaded with CAN approximately within 30 minutes of hydrolysis and mixed gently with the liquid growth media (BHI) containing cells and 1% sucrose. A stock solution of CAN was analyzed via Dynamic Light Scattering (DLS), approximately 10-30 minutes after hydrolysis at room temperature. supporting the previous report by Pettinger et al. (20) The UV-Vis absorption spectrum of CAN (NanoDrop™ 2000/2000c, Thermo Fisher) in $H_2O$ was in agreement with literature, with a well-defined shoulder peak at 290 nm that intensifies significantly upon standing in solution over several hours (20) (FIG. 11).

A stock solution of ceric ammonium sulfate dihydrate (Acros, 15.8 mgs) (CAS) (5 mmol Ce) was prepared and analyzed via DLS as described above. The hydrolysis of CAS yielded particles with low scattering counts and a size range extending below the lower detection limit of the instrument. The UV-Vis Absorption spectrum of CAS in $H_2O$ did not have a well-defined peak at 290 nm as with CAN. Instead, a broadened peak with an absorption maximum at 275 nm (FIG. 11) was observed. This peak did not significantly increase in intensity over time.

In Vitro Biofilm Assays and Light Microscopy.

Figure 12:
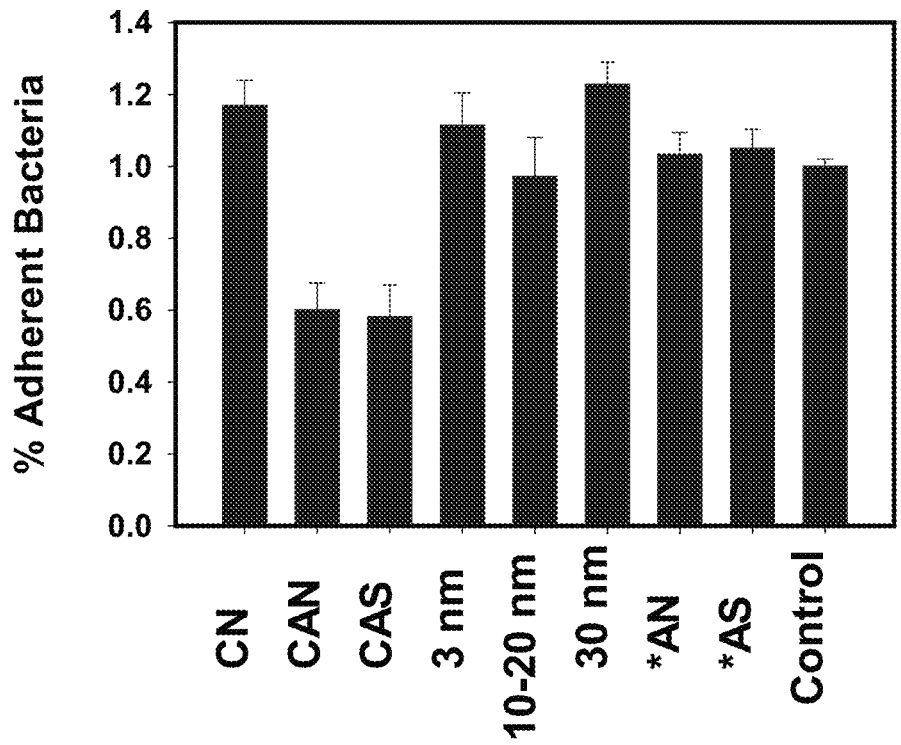
FIG. 12 shows a graph that can demonstrate the results from in vitro screening of cerium containing agents (125 µM Ce) and ammonium salts (*1 mM) in static biofilm inhibition assays with S. mutans UA159. Growth conditions: BHI, 1% sucrose, 37° C., 5% $CO_2$ for 20 hrs.

An overnight culture of *S. mutans* UA159 was diluted and grown to exponential growth phase (OD600=0.5-0.6) in Brain Heart Infusion (BHI) growth media. The cells were diluted 40-fold into a BHI/1% sucrose solution and transferred to a 96-well, tissue cultured, polystyrene microtiter plate. 5 mM aqueous stock solutions of cerium nitrate hexahydrate (CN), ceric ammonium nitrate (CAN), ceric ammonium sulfate (CAS), 3 nm $CeO_2$-NP (3 nm) (Strem), 10-20 nm $CeO_2$-NP (10-20 nm) (Alfa Aesar) 30 nm $CeO_2$-NP (30 nm) (Alfa Aesar) were freshly prepared, and vortexed prior to testing inhibitory activity. 40 mM stock solutions of ammonium nitrate (AN) and ammonium sulfate (AS) were also prepared. The wells of the microtiter plate were inoculated with freshly diluted *S. mutans* BHI (1% sucrose) and each appropriate stock solution to afford 125 µM Ce, 1 mM NH4NO3 and 1 mM $(NH_4)_2SO_4$ as shown in FIG. 12, to a total volume of 200 µL in each well. The wells were mixed gently with a microchannel pipette following addition of each agent. Both experimental and control wells were set up with 6 replicates. The microtiter plate was then placed in an incubator under the following conditions: 37° C., 5% $CO_2$ for 20 hours. Following the 20-hr incubation time, the plates were gently submerged in a water bath 3-4 times to remove excess non-adherent cells and cellular debris. Each well was then stained with 200 µL of 0.1% crystal violet stain for approximately 30 minutes at 37° C. The microtiter plate was then gently re-submerged (washed) in a water bath, to remove excess dye and dry for a minimum of 24 hrs. The dyed contents of each well were re-dissolved in 33% acetic acid with repeated mixing and diluted appropriately in aqueous solution. The absorbance of each well at 570 nm was then recorded with a Victor3v plate reader, and the average absorbance of the six replicates were plotted below. The positive control was taken as 100% biofilm formation, and the negative control absorbance at 570 was subtracted from the absorbance of all experimental wells. The percent absorbance of 100% biofilm formation (the positive control) is plotted in FIG. 12. Error bars represent the standard deviation of the percent inhibition values of the six replicates.

Lab-Tek® Chamber slide (8-well Permacol® Slide) was inoculated with *S. mutans* (BHI, 1% sucrose) in a manner similar as described above. The wells were setup in duplicate, incorporating positive and negative controls, as well as 125 µM and 250 µM CAS treated wells at a volume of 400 µL. After 20 hrs of incubation at 37° C., 5% $CO_2$, the chamber slide was rinsed gently in a water bath to remove nonadherent cellular debris. Each well was then stained with 400 µL FilmTracer™ SYPRO® Ruby Biofilm matrix stain according to the manufacturer's protocol. The chamber slide was then rinsed gently and the chamber components were removed to allow visualization of the microscopic slide. 30 µL of sterilized water was added to each well and then a coverslip was placed. The slide was then viewed under a Nikon Eclipse E600 microscope at 10× magnification utilizing a TRITC emission filter.

Dose-Response Study

The same protocol for the culturing *S. mutans* UA159, dilutions and inoculation of a 96-well microtiter polystyrene plate was followed as described above. A 5 mM stock solution of ceric ammonium nitrate was freshly prepared within 30 minutes of addition to wells. The final volume of each well (test and controls) was 200 µL. Both test wells and controls were run with 6 replicates. The loaded microtiter plate was placed in an incubator at 37° C., 5% $CO_2$ for 20 hr. The same workup described above for removing non-adherent cells/debris, staining with 0.1% CV, quantification of retained crystal violet stain on the Victor3v plate reader was followed to generate the dose response curve shown below. The positive control was taken as 0% inhibition. Each data point below represents the average percent inhibition of the six replicates, and the error bar represents the standard deviation of the percent inhibition of the six replicates. The data was fit to the Hill equation (3-parameter) to arrive at the $IC_{50}$ value reported below. SigmaPlot 12.0 was used to fit the data to a single rectangular hyperbolic curve to determine KD values. The hyperbolic equation, y=ymax·x/(KD+x), was used to plot response units and corresponding concentration, where y is the response, ymax is the maximum response, and x is the concentration (Equation 2).

$$\% \text{ Inhibition} = \frac{(\text{Positive Control Absorbance}) - (\text{Test well Absorbance})}{(\text{Positive Control Absorbance})} \times 100 \quad (\text{Eq. 2})$$

REFERENCES FOR EXAMPLE 3

1. Lewandowski Z, Beyenal H. Fundamentals of biofilm research. Second edition. ed. Boca Raton: CRC Press, Taylor & Francis Group; 2014. xxi, 642 pages p.
2. Algburi A, Comito N, Kashtanov D, Dicks L M, Chikindas M L. Control of Biofilm Formation: Antibiotics and Beyond. Appl Environ Microbiol. 2017; 83(3). doi: 10.1128/AEM.02508-16. PubMed PMID: 27864170; PMCID: 5244297.
3. Davies D. Understanding biofilm resistance to antibacterial agents. Nat Rev Drug Discov. 2003; 2(2):114-22. doi: 10.1038/nrd1008. PubMed PMID: 12563302.
4. Dewhirst F E, Chen T, Izard J, Paster B J, Tanner A C, Yu W H, Lakshmanan A, Wade W G. The human oral microbiome. J Bacteriol. 2010; 192(19):5002-17. doi: 10.1128/JB.00542-10. PubMed PMID: 20656903; PMCID: 2944498.
5. Heller D, Helmerhorst E J, Gower A C, Siqueira W L, Paster B J, Oppenheim F G. Microbial Diversity in the Early In Vivo-Formed Dental Biofilm. Appl Environ Microbiol. 2016; 82(6):1881-8. doi: 10.1128/AEM.03984-15. PubMed PMID: 26746720; PMCID: 4784052.
6. Klein M I, Hwang G, Santos P H, Campanella O H, Koo H. *Streptococcus mutans*-derived extracellular matrix in cariogenic oral biofilms. Front Cell Infect Microbiol. 2015; 5:10. doi: 10.3389/fcimb.2015.00010. PubMed PMID: 25763359; PMCID: 4327733.
7. Ferretti J J, Ward M. Susceptibility of *Streptococcus mutans* to antimicrobial agents. Antimicrob Agents Chemother. 1976; 10(2):274-6. PubMed PMID: 984768; PMCID: 429734.
8. Davis I J, Richards H, Mullany P. Isolation of silver- and antibiotic-resistant *Enterobacter cloacae* from teeth. Oral Microbiol Immunol. 2005; 20(3):191-4. doi: 10.1111/j.1399-302X.2005.00218.x. PubMed PMID: 15836522.
9. Mijnendonckx K, Leys N, Mahillon J, Silver S, Van Houdt R. Antimicrobial silver: uses, toxicity and potential for resistance. Biometals. 2013; 26(4):609-21. doi: 10.1007/s10534-013-9645-z. PubMed PMID: 23771576.
10. Rabin N, Zheng Y, Opoku-Temeng C, Du Y, Bonsu E, Sintim H O. Agents that inhibit bacterial biofilm formation. Future Med Chem. 2015; 7(5):647-71. doi: 10.4155/fmc.15.7. PubMed PMID: 25921403.
11. Allaker R P, Memarzadeh K. Nanoparticles and the control of oral infections. Int J Antimicrob Agents. 2014; 43(2):95-104. doi: 10.1016/j.ijantimicag.2013.11.002. PubMed PMID: 24388116.
12. Hannig M, Hannig C. Nanomaterials in preventive dentistry. Nat Nanotechnol. 2010; 5(8):565-9. doi: 10.1038/nnano.2010.83. PubMed PMID: 20581832.
13. Rajeshkumar S, Naik P. Synthesis and biomedical applications of Cerium oxide nanoparticles—A Review. Biotechnol Rep (Amst). 2018; 17:1-5. doi: 10.1016/j.btre.2017.11.008. PubMed PMID: 29234605; PMCID: 5723353.
14. Pelletier D A, Suresh A K, Holton G A, McKeown C K, Wang W, Gu B, Mortensen N P, Allison D P, Joy D C, Allison M R, Brown S D, Phelps T J, Doktycz M J. Effects of engineered cerium oxide nanoparticles on bacterial growth and viability. Appl Environ Microbiol. 2010; 76(24):7981-9. doi: 10.1128/AEM.00650-10. PubMed PMID: 20952651; PMCID: 3008265.
15. Farias I A P, Dos Santos C C L, Sampaio F C. Antimicrobial Activity of Cerium Oxide Nanoparticles on Opportunistic Microorganisms: A Systematic Review. Biomed Res Int. 2018; 2018:1923606. doi: 10.1155/2018/1923606. PubMed PMID: 29607315; PMCID: 5827881.
16. Masadeh M M, Karasneh G A, Al-Akhras M A, Albiss B A, Aljarah K M, Al-Azzam S I, Alzoubi K H. Cerium oxide and iron oxide nanoparticles abolish the antibacterial activity of ciprofloxacin against gram positive and gram negative biofilm bacteria. Cytotechnology. 2015; 67(3):427-35. doi: 10.1007/s10616-014-9701-8. PubMed PMID: 24643389; PMCID: 4371563.
17. Xu Y, Wang C, Hou J, Wang P, You G, Miao L. Mechanistic understanding of cerium oxide nanoparticle-mediated biofilm formation in *Pseudomonas aeruginosa*. Environ Sci Pollut Res Int. 2018; 25(34):34765-76. doi: 10.1007/s11356-018-3418-8. PubMed PMID: 30324376.
18. Nabavi M, Spalla O, Cabane B. Surface-Chemistry of Nanometric Ceria Particles in Aqueous Dispersions. J Colloid Interf Sci. 1993; 160(2):459-71. doi: DOI 10.1006/jcis.1993.1417. PubMed PMID: WOS: A1993MA31400022.
19. Xu J X, Li G S, Li L P. CeO2 nanocrystals: Seed-mediated synthesis and size control. Mater Res Bull. 2008; 43(4):990-5. doi: 10.1016/j.materresbull.2007.04.019. PubMed PMID: WOS: 000255082300027.
20. Pettinger N W, Williams R E, Chen J, Kohler B. Crystallization kinetics of cerium oxide nanoparticles formed by spontaneous, room-temperature hydrolysis of cerium(iv) ammonium nitrate in light and heavy water. Phys Chem Chem Phys. 2017; 19(5):3523-31. doi: 10.1039/c6cp08227k. PubMed PMID: 28094375.
21. Demars T J, Bera M K, Seifert S, Antonio M R, Ellis R J. Revisiting the solution structure of ceric ammonium nitrate. Angew Chem Int Ed Engl. 2015; 54(26):7534-8. doi: 10.1002/anie.201502336. PubMed PMID: 25906967.
22. O'Toole G A. Microtiter dish biofilm formation assay. J Vis Exp. 2011(47). doi: 10.3791/2437. PubMed PMID: 21307833; PMCID: 3182663.
23. Cobrado L, Silva-Dias A, Azevedo M M, Pina-Vaz C, Rodrigues A G. In vivo antibiofilm effect of cerium, chitosan and hamamelitannin against usual agents of catheter-related bloodstream infections. J Antimicrob Chemother. 2013; 68(1):126-30. doi: 10.1093/jac/dks376. PubMed PMID: 22991425.

24. Cobrado L, Azevedo M M, Silva-Dias A, Ramos J P, Pina-Vaz C, Rodrigues A G. Cerium, chitosan and hamamelitannin as novel biofilm inhibitors? J Antimicrob Chemother. 2012; 67(5):1159-62. doi: 10.1093/jac/dks007. PubMed PMID: 22316569.
25. Silva-Dias A, Miranda I M, Branco J, Cobrado L, Monteiro-Soares M, Pina-Vaz C, Rodrigues A G. In vitro antifungal activity and in vivo antibiofilm activity of cerium nitrate against *Candida* species. J Antimicrob Chemother. 2016; 71(3):848. doi: 10.1093/jac/dkv469. PubMed PMID: 26747097.
26. Ren Z, Chen L, Li J, Li Y. Inhibition of *Streptococcus mutans* polysaccharide synthesis by molecules targeting glycosyltransferase activity. J Oral Microbiol. 2016; 8:31095. doi: 10.3402/jom.v8.31095. PubMed PMID: 27105419; PMCID: 4841093.

I claim:

1. A formulation comprising:
an effective amount of a hydrolyzed tetravalent metal salt nanoparticle that inhibits biofilm formation, wherein the hydrolyzed tetravalent metal salt is a hydrolysis product of a Ce(IV) salt, a Zr(IV) salt, or a Ti(IV) salt.

2. The formulation of claim 1, wherein the hydrolyzed tetravalent metal salt is a hydrolysis product of Ce(IV) salt.

3. The formulation of claim 1, wherein the hydrolyzed tetravalent metal salt is $CeO_2$.

4. The formulation of claim 3, wherein the nanoparticles have an average hydrodynamic radius of about 2 nm to about 10 nm.

5. The formulation of claim 1, further comprising an additional metal salt selected from the group consisting of: salts of Ca(II), Sr(II), Ba(II), Zn(II), Cu(II), Be(II), Ni(II), Fe(II), Co(II), Mn(II), Cr(II), V(II), Ti(II), Sc(II), Cd(II), Hg(II), cacodylic acid (As) sodium salt, and any combination thereof.

6. A method of inhibiting a biofilm in a subject in need thereof, the method comprising:
administering to the subject in need thereof an amount of a pharmaceutical formulation comprising:
the formulation of claim 1; and
a pharmaceutically acceptable carrier.

7. The method of claim 6, wherein the pharmaceutical formulation further comprises an additional metal salt selected from the group consisting of: salts of Ca(II), Sr(II), Ba(II), Zn(II), Cu(II), Be(II), Ni(II), Fe(II), Co(II), Mn(II), Cr(II), V(II), Ti(II), Sc(II), Cd(II), Hg(II), cacodylic acid (As) sodium salt, and any combination thereof.

8. A medical device comprising:
one or more surfaces partially or completely coated with the formulation of claim 1.

9. The medical device of claim 8, wherein the formulation further comprises an additional metal salt selected from the group consisting of: salts of Ca(II), Sr(II), Ba(II), Zn(II), Cu(II), Be(II), Ni(II), Fe(II), Co(II), Mn(II), Cr(II), V(II), Ti(II), Sc(II), Cd(II), Hg(II), cacodylic acid (As) sodium salt, and any combination thereof.

10. The formulation of claim 1, wherein the formulation comprises an oral formulation.

11. The formulation of claim 10, wherein the formulation comprises a foam, spray, lozenge, pastille, mouth wash, mouth rinse, or paste.

12. The formulation of claim 10, wherein the formulation comprises nanoparticles of $CeO_2$ having an average hydrodynamic radius of about 2 nm to about 10 nm.

13. The formulation of claim 10, wherein the hydrolyzed tetravalent metal salt has a dosage of from about 1 picogram to 10 grams.

14. The formulation of claim 1, wherein the formulation further comprises a pharmaceutically acceptable carrier.

15. The formulation of claim 14, wherein the pharmaceutically acceptable carrier comprises water, a salt solution, an alcohol, gum arabic, a vegetable oil, a benzyl alcohol, a polyethylene glycol, gelatin, a carbohydrate, magnesium stearate, talc, silicic acid, a viscous paraffin, a perfume oil, a fatty acid ester, a hydroxy methylcellulose, or polyvinyl pyrrolidone.

16. The formulation of claim 14, wherein the pharmaceutically acceptable carrier comprises a carbohydrate.

17. The formulation of claim 1, wherein the nanoparticle is coated.

18. The formulation of claim 17, wherein the coating comprises a cellulose polymer, polyvinyl acetate phthalate, an acrylic acid polymer and copolymer, or a methacrylic resin.

* * * * *